(12) United States Patent
Mano et al.

(10) Patent No.: US 8,748,145 B2
(45) Date of Patent: Jun. 10, 2014

(54) MUTANTS OF PYRROLOQUINOLINE QUININE-DEPENDENT SOLUBLE GLUCOSE DEHYDROGENASE

(75) Inventors: Nicolas Mano, Talence (FR); Claire Stines-Chaumeil, Talence (FR); Fabien Durand, Bordeaux (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 64 days.

(21) Appl. No.: 13/387,514

(22) PCT Filed: Jul. 20, 2010

(86) PCT No.: PCT/FR2010/000522
§ 371 (c)(1),
(2), (4) Date: Mar. 23, 2012

(87) PCT Pub. No.: WO2011/012779
PCT Pub. Date: Feb. 3, 2011

(65) Prior Publication Data
US 2012/0178115 A1 Jul. 12, 2012

(30) Foreign Application Priority Data
Jul. 28, 2009 (FR) .................................. 09 03694

(51) Int. Cl.
| | | |
|---|---|---|
| C12N 9/04 | (2006.01) | |
| C12Q 1/54 | (2006.01) | |
| C12P 21/06 | (2006.01) | |
| C12P 19/34 | (2006.01) | |
| C12N 15/00 | (2006.01) | |
| C12N 1/20 | (2006.01) | |
| C07H 21/04 | (2006.01) | |
| C07K 1/00 | (2006.01) | |
| B23H 3/04 | (2006.01) | |
| C12M 1/00 | (2006.01) | |
| G01F 1/64 | (2006.01) | |

(52) U.S. Cl.
USPC ........... 435/190; 435/14; 435/69.1; 435/91.1; 435/320.1; 435/252.33; 536/23.1; 536/23.2; 530/350; 204/290.01; 204/403.01; 205/782

(58) Field of Classification Search
None
See application file for complete search history.

(56) References Cited

U.S. PATENT DOCUMENTS

| | | |
|---|---|---|
| 7,037,689 B2 | 5/2006 | Bathe et al. |
| 7,132,270 B2 | 11/2006 | Kratzsch et al. |
| 7,244,581 B2 | 7/2007 | Sode |
| 2003/0104595 A1 | 6/2003 | Kratzch et al. |
| 2003/0232418 A1 | 12/2003 | Takeshima et al. |
| 2006/0148056 A1 | 7/2006 | Kratzsch et al. |
| 2007/0105173 A1 | 5/2007 | Takeshima et al. |
| 2007/0243566 A1 | 10/2007 | Boenitz-Dulat et al. |

FOREIGN PATENT DOCUMENTS

| | | | |
|---|---|---|---|
| WO | WO 2006/040172 A1 * | 4/2006 | ............... C12N 9/04 |
| WO | WO 2006/085509 | 8/2006 | |

OTHER PUBLICATIONS

Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
International Search Report for PCT/FR2010/000522, Apr. 10, 2010.

* cited by examiner

*Primary Examiner* — Ganapathirama Raghu
(74) *Attorney, Agent, or Firm* — B. Aaron Schulman, Esq.; Stites & Harbison PLLC

(57) ABSTRACT

The present invention relates to novel mutants of PQQ s-GDH containing an amino acid substitution in position 428 of the protein sequence of the wild type PQQ s-GDH of *Acinetobacter calcoaceticus* (SEQ.ID. NO:2). The invention also relates to the use of said PQQ s-GDH mutants for the development of glucose electrodes of interest in the assay of glucose, in particular of blood glucose in diabetic subjects, and for implementing biofuel cells that utilize glucose as fuel.

11 Claims, 7 Drawing Sheets

SEQUENCE LISTING

<160> NUMBER OF SEQ ID NOS: 26

<210> SEQ ID NO 1
<211> LENGTH: 1389
<212> TYPE: DNA
<213> ORGANISM: Acinetobacter calcoaceticus
<220> FEATURE:
<221> NAME/KEY: CDS
<222> LOCATION: (1)..(1389)

<400> SEQUENCE: 1

```
gat gtt cct cta act cca tct caa ttt gct aaa gcg aaa tca gag aac      48
Asp Val Pro Leu Thr Pro Ser Gln Phe Ala Lys Ala Lys Ser Glu Asn
1               5                   10                  15 ttt gac aag aaa gtt att cta tct aat cta aat aag ccg cat gct ttg      96
Phe Asp Lys Lys Val Ile Leu Ser Asn Leu Asn Lys Pro His Ala Leu
            20                  25                  30 tta tgg gga cca gat aat caa att tgg tta act gag cga gca aca ggt     144
Leu Trp Gly Pro Asp Asn Gln Ile Trp Leu Thr Glu Arg Ala Thr Gly
        35                  40                  45 aag att cta aga gtt aat cca gag tcg ggt agt gta aaa aca gtt ttt     192
Lys Ile Leu Arg Val Asn Pro Glu Ser Gly Ser Val Lys Thr Val Phe
    50                  55                  60
```

```
cag gta cca gag att gtc aat gat gct gat ggg cag aat ggt tta tta      240
Gln Val Pro Glu Ile Val Asn Asp Ala Asp Gly Gln Asn Gly Leu Leu
 65              70                  75                  80 ggt ttt gcc ttc cat cct gat ttt aaa aat aat cct tat atc tat att      288
Gly Phe Ala Phe His Pro Asp Phe Lys Asn Asn Pro Tyr Ile Tyr Ile
                 85                  90                  95 tca ggt aca ttt aaa aat ccg aaa tct aca gat aaa gaa tta ccg aac      336
Ser Gly Thr Phe Lys Asn Pro Lys Ser Thr Asp Lys Glu Leu Pro Asn
                100                 105                 110 caa acg att att cgt cgt tat acc tat aat aaa tca aca gat acg ctc      384
Gln Thr Ile Ile Arg Arg Tyr Thr Tyr Asn Lys Ser Thr Asp Thr Leu
            115                 120                 125 gag aag cca gtc gat tta tta gca gga tta cct tca tca aaa gac cat      432
Glu Lys Pro Val Asp Leu Leu Ala Gly Leu Pro Ser Ser Lys Asp His
        130                 135                 140 cag tca ggt cgt ctt gtc att ggg cca gat caa aag att tat tat acg      480
Gln Ser Gly Arg Leu Val Ile Gly Pro Asp Gln Lys Ile Tyr Tyr Thr
145                 150                 155                 160 att ggt gac caa ggg cgt aac cag ctt gct tat ttg ttc ttg cca aat      528
Ile Gly Asp Gln Gly Arg Asn Gln Leu Ala Tyr Leu Phe Leu Pro Asn
                165                 170                 175 caa gca caa cat acg cca act caa caa gaa ctg aat ggt aaa gac tat      576
Gln Ala Gln His Thr Pro Thr Gln Gln Glu Leu Asn Gly Lys Asp Tyr
            180                 185                 190 cac acc tat atg ggt aaa gta cta cgc tta aat ctt gat gga agt att      624
His Thr Tyr Met Gly Lys Val Leu Arg Leu Asn Leu Asp Gly Ser Ile
        195                 200                 205 cca aag gat aat cca agt ttt aac ggg gtg gtt agc cat att tat aca      672
Pro Lys Asp Asn Pro Ser Phe Asn Gly Val Val Ser His Ile Tyr Thr
    210                 215                 220 ctt gga cat cgt aat ccg cag ggc tta gca ttc act cca aat ggt aaa      720
Leu Gly His Arg Asn Pro Gln Gly Leu Ala Phe Thr Pro Asn Gly Lys
225                 230                 235                 240 tta ttg cag tct gaa caa ggc cca aac tct gac gat gaa att aac ctc      768
Leu Leu Gln Ser Glu Gln Gly Pro Asn Ser Asp Asp Glu Ile Asn Leu
                245                 250                 255 att gtc aaa ggt ggc aat tat ggt tgg ccg aat gta gca ggt tat aaa      816
Ile Val Lys Gly Gly Asn Tyr Gly Trp Pro Asn Val Ala Gly Tyr Lys
            260                 265                 270 gat gat agt ggc tat gct tat gca aat tat tca gca gca gcc aat aag      864
Asp Asp Ser Gly Tyr Ala Tyr Ala Asn Tyr Ser Ala Ala Ala Asn Lys
        275                 280                 285 tca att aag gat tta gct caa aat gga gta aaa gta gcc gca ggg gtc      912
Ser Ile Lys Asp Leu Ala Gln Asn Gly Val Lys Val Ala Ala Gly Val
    290                 295                 300 cct gtg acg aaa gaa tct gaa tgg act ggt aaa aac ttt gtc cca cca      960
Pro Val Thr Lys Glu Ser Glu Trp Thr Gly Lys Asn Phe Val Pro Pro
305                 310                 315                 320 tta aaa act tta tat acc gtt caa gat acc tac aac tat aac gat cca     1008
Leu Lys Thr Leu Tyr Thr Val Gln Asp Thr Tyr Asn Tyr Asn Asp Pro
                325                 330                 335 act tgt gga gag atg acc tac att tgc tgg cca aca gtt gca ccg tca     1056
Thr Cys Gly Glu Met Thr Tyr Ile Cys Trp Pro Thr Val Ala Pro Ser
            340                 345                 350 tct gcc tat gtc tat aag ggc ggt aaa aaa gca att act ggt tgg gaa     1104
Ser Ala Tyr Val Tyr Lys Gly Gly Lys Lys Ala Ile Thr Gly Trp Glu
        355                 360                 365 aat aca tta ttg gtt cca tct tta aaa cgt ggt gtc att ttc cgt att     1152
Asn Thr Leu Leu Val Pro Ser Leu Lys Arg Gly Val Ile Phe Arg Ile
    370                 375                 380
```

```
aag tta gat cca act tat agc act act tat gat gac gct gta ccg atg      1200
Lys Leu Asp Pro Thr Tyr Ser Thr Thr Tyr Asp Asp Ala Val Pro Met
385                 390                 395                 400 ttt aag agc aac aac cgt tat cgt gat gtg att gca agt cca gat ggg      1248
Phe Lys Ser Asn Asn Arg Tyr Arg Asp Val Ile Ala Ser Pro Asp Gly
            405                 410                 415 aat gtc tta tat gta tta act gat act gcc gga aat gtc caa aaa gat      1296
Asn Val Leu Tyr Val Leu Thr Asp Thr Ala Gly Asn Val Gln Lys Asp
        420                 425                 430 gat ggc tca gta aca aat aca tta gaa aac cca gga tct ctc att aag      1344
Asp Gly Ser Val Thr Asn Thr Leu Glu Asn Pro Gly Ser Leu Ile Lys
    435                 440                 445 ttc acc tat aag gct aag taa tac agt cgc att aaa aaa ccg atc          1389
Phe Thr Tyr Lys Ala Lys     Tyr Ser Arg Ile Lys Lys Pro Ile
450                 455                 460

<210> SEQ ID NO 2
<211> LENGTH: 454
<212> TYPE: PRT
<213> ORGANISM: Acinetobacter calcoaceticus

<400> SEQUENCE: 2

Asp Val Pro Leu Thr Pro Ser Gln Phe Ala Lys Ala Lys Ser Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ser Thr Asp Thr Leu
        115                 120                 125

Glu Lys Pro Val Asp Leu Leu Ala Gly Leu Pro Ser Ser Lys Asp His
130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270
```

```
Asp Asp Ser Gly Tyr Ala Tyr Ala Asn Tyr Ser Ala Ala Asn Lys
        275                 280                 285

Ser Ile Lys Asp Leu Ala Gln Asn Gly Val Lys Val Ala Ala Gly Val
    290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
                325                 330                 335

Thr Cys Gly Glu Met Thr Tyr Ile Cys Trp Pro Thr Val Ala Pro Ser
                340                 345                 350

Ser Ala Tyr Val Tyr Lys Gly Gly Lys Lys Ala Ile Thr Gly Trp Glu
                355                 360                 365

Asn Thr Leu Leu Val Pro Ser Leu Lys Arg Gly Val Ile Phe Arg Ile
        370                 375                 380

Lys Leu Asp Pro Thr Tyr Ser Thr Thr Tyr Asp Asp Ala Val Pro Met
385                 390                 395                 400

Phe Lys Ser Asn Asn Arg Tyr Arg Asp Val Ile Ala Ser Pro Asp Gly
                405                 410                 415

Asn Val Leu Tyr Val Leu Thr Asp Thr Ala Gly Asn Val Gln Lys Asp
                420                 425                 430

Asp Gly Ser Val Thr Asn Thr Leu Glu Asn Pro Gly Ser Leu Ile Lys
                435                 440                 445

Phe Thr Tyr Lys Ala Lys
        450

<210> SEQ ID NO 3
<211> LENGTH: 1389
<212> TYPE: DNA
<213> ORGANISM: Acinetobacter calcoaceticus
<220> FEATURE:
<221> NAME/KEY: CDS
<222> LOCATION: (1)..(1389)

<400> SEQUENCE: 3 gat gtt cct cta act cca tct caa ttt gct aaa gcg aaa tca gag aac    48
Asp Val Pro Leu Thr Pro Ser Gln Phe Ala Lys Ala Lys Ser Glu Asn
1               5                   10                  15 ttt gac aag aaa gtt att cta tct aat cta aat aag ccg cat gct ttg    96
Phe Asp Lys Lys Val Ile Leu Ser Asn Leu Asn Lys Pro His Ala Leu
            20                  25                  30 tta tgg gga cca gat aat caa att tgg tta act gag cga gca aca ggt   144
Leu Trp Gly Pro Asp Asn Gln Ile Trp Leu Thr Glu Arg Ala Thr Gly
        35                  40                  45 aag att cta aga gtt aat cca gag tcg ggt agt gta aaa aca gtt ttt   192
Lys Ile Leu Arg Val Asn Pro Glu Ser Gly Ser Val Lys Thr Val Phe
    50                  55                  60 cag gta cca gag att gtc aat gat gct gat ggg cag aat ggt tta tta   240
Gln Val Pro Glu Ile Val Asn Asp Ala Asp Gly Gln Asn Gly Leu Leu
65                  70                  75                  80 ggt ttt gcc ttc cat cct gat ttt aaa aat aat cct tat atc tat att   288
Gly Phe Ala Phe His Pro Asp Phe Lys Asn Asn Pro Tyr Ile Tyr Ile
                85                  90                  95 tca ggt aca ttt aaa aat ccg aaa tct aca gat aaa gaa tta ccg aac   336
Ser Gly Thr Phe Lys Asn Pro Lys Ser Thr Asp Lys Glu Leu Pro Asn
            100                 105                 110 caa acg att att cgt cgt tat acc tat aat aaa tca aca gat acg ctc   384
Gln Thr Ile Ile Arg Arg Tyr Thr Tyr Asn Lys Ser Thr Asp Thr Leu
        115                 120                 125 gag aag cca gtc gat tta tta gca gga tta cct tca tca aaa gac cat   432
```

```
            Glu Lys Pro Val Asp Leu Leu Ala Gly Leu Pro Ser Ser Lys Asp His
                130                 135                 140 cag tca ggt cgt ctt gtc att ggg cca gat caa aag att tat tat acg          480
Gln Ser Gly Arg Leu Val Ile Gly Pro Asp Gln Lys Ile Tyr Tyr Thr
145                 150                 155                 160 att ggt gac caa ggg cgt aac cag ctt gct tat ttg ttc ttg cca aat          528
Ile Gly Asp Gln Gly Arg Asn Gln Leu Ala Tyr Leu Phe Leu Pro Asn
                165                 170                 175 caa gca caa cat acg cca act caa caa gaa ctg aat ggt aaa gac tat          576
Gln Ala Gln His Thr Pro Thr Gln Gln Glu Leu Asn Gly Lys Asp Tyr
                180                 185                 190 cac acc tat atg ggt aaa gta cta cgc tta aat ctt gat gga agt att          624
His Thr Tyr Met Gly Lys Val Leu Arg Leu Asn Leu Asp Gly Ser Ile
            195                 200                 205 cca aag gat aat cca agt ttt aac ggg gtg gtt agc cat att tat aca          672
Pro Lys Asp Asn Pro Ser Phe Asn Gly Val Val Ser His Ile Tyr Thr
    210                 215                 220 ctt gga cat cgt aat ccg cag ggc tta gca ttc act cca aat ggt aaa          720
Leu Gly His Arg Asn Pro Gln Gly Leu Ala Phe Thr Pro Asn Gly Lys
225                 230                 235                 240 tta ttg cag tct gaa caa ggc cca aac tct gac gat gaa att aac ctc          768
Leu Leu Gln Ser Glu Gln Gly Pro Asn Ser Asp Asp Glu Ile Asn Leu
                245                 250                 255 att gtc aaa ggt ggc aat tat ggt tgg ccg aat gta gca ggt tat aaa          816
Ile Val Lys Gly Gly Asn Tyr Gly Trp Pro Asn Val Ala Gly Tyr Lys
                260                 265                 270 gat gat agt ggc tat gct tat gca aat tat tca gca gca gcc aat aag          864
Asp Asp Ser Gly Tyr Ala Tyr Ala Asn Tyr Ser Ala Ala Ala Asn Lys
            275                 280                 285 tca att aag gat tta gct caa aat gga gta aaa gta gcc gca ggg gtc          912
Ser Ile Lys Asp Leu Ala Gln Asn Gly Val Lys Val Ala Ala Gly Val
    290                 295                 300 cct gtg acg aaa gaa tct gaa tgg act ggt aaa aac ttt gtc cca cca          960
Pro Val Thr Lys Glu Ser Glu Trp Thr Gly Lys Asn Phe Val Pro Pro
305                 310                 315                 320 tta aaa act tta tat acc gtt caa gat acc tac aac tat aac gat cca         1008
Leu Lys Thr Leu Tyr Thr Val Gln Asp Thr Tyr Asn Tyr Asn Asp Pro
                325                 330                 335 act tgt gga gag atg acc tac att tgc tgg cca aca gtt gca ccg tca         1056
Thr Cys Gly Glu Met Thr Tyr Ile Cys Trp Pro Thr Val Ala Pro Ser
                340                 345                 350 tct gcc tat gtc tat aag ggc ggt aaa aaa gca att act ggt tgg gaa         1104
Ser Ala Tyr Val Tyr Lys Gly Gly Lys Lys Ala Ile Thr Gly Trp Glu
            355                 360                 365 aat aca tta ttg gtt cca tct tta aaa cgt ggt gtc att ttc cgt att         1152
Asn Thr Leu Leu Val Pro Ser Leu Lys Arg Gly Val Ile Phe Arg Ile
    370                 375                 380 aag tta gat cca act tat agc act act tat gat gac gct gta ccg atg         1200
Lys Leu Asp Pro Thr Tyr Ser Thr Thr Tyr Asp Asp Ala Val Pro Met
385                 390                 395                 400 ttt aag agc aac aac cgt tat cgt gat gtg att gca agt cca gat ggg         1248
Phe Lys Ser Asn Asn Arg Tyr Arg Asp Val Ile Ala Ser Pro Asp Gly
                405                 410                 415 aat gtc tta tat gta tta act gat act gcc gga tgt gtc caa aaa gat         1296
Asn Val Leu Tyr Val Leu Thr Asp Thr Ala Gly Cys Val Gln Lys Asp
                420                 425                 430 gat ggc tca gta aca aat aca tta gaa aac cca gga tct ctc att aag         1344
Asp Gly Ser Val Thr Asn Thr Leu Glu Asn Pro Gly Ser Leu Ile Lys
            435                 440                 445 ttc acc tat aag gct aag taa tac agt cgc att aaa aaa ccg atc             1389
```

```
Phe Thr Tyr Lys Ala Lys     Tyr Ser Arg Ile Lys Lys Pro Ile
        450                 455             460
```

<210> SEQ ID NO 4
<211> LENGTH: 454
<212> TYPE: PRT
<213> ORGANISM: Acinetobacter calcoaceticus

<400> SEQUENCE: 4

```
Asp Val Pro Leu Thr Pro Ser Gln Phe Ala Lys Ala Lys Ser Glu Asn
 1               5                  10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ser Thr Asp Thr Leu
        115                 120                 125

Glu Lys Pro Val Asp Leu Leu Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
    210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Ala Asn Lys
        275                 280                 285

Ser Ile Lys Asp Leu Ala Gln Asn Gly Val Lys Val Ala Ala Gly Val
    290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
                325                 330                 335

Thr Cys Gly Glu Met Thr Tyr Ile Cys Trp Pro Thr Val Ala Pro Ser
            340                 345                 350

Ser Ala Tyr Val Tyr Lys Gly Gly Lys Lys Ala Ile Thr Gly Trp Glu
        355                 360                 365
```

-continued

| | | | | | | | | | | | | | |
|---|---|---|---|---|---|---|---|---|---|---|---|---|---|
| Asn | Thr | Leu | Leu | Val | Pro | Ser | Leu | Lys | Arg | Gly | Val | Ile | Phe | Arg | Ile |
| | 370 | | | | 375 | | | | | 380 | | | | | |

| Lys | Leu | Asp | Pro | Thr | Tyr | Ser | Thr | Thr | Tyr | Asp | Asp | Ala | Val | Pro | Met |
|---|---|---|---|---|---|---|---|---|---|---|---|---|---|---|---|
| 385 | | | | | 390 | | | | | 395 | | | | | 400 |

| Phe | Lys | Ser | Asn | Asn | Arg | Tyr | Arg | Asp | Val | Ile | Ala | Ser | Pro | Asp | Gly |
|---|---|---|---|---|---|---|---|---|---|---|---|---|---|---|---|
| | | | | 405 | | | | | 410 | | | | | 415 | |

| Asn | Val | Leu | Tyr | Val | Leu | Thr | Asp | Thr | Ala | Gly | Cys | Val | Gln | Lys | Asp |
|---|---|---|---|---|---|---|---|---|---|---|---|---|---|---|---|
| | | | 420 | | | | | 425 | | | | | 430 | | |

| Asp | Gly | Ser | Val | Thr | Asn | Thr | Leu | Glu | Asn | Pro | Gly | Ser | Leu | Ile | Lys |
|---|---|---|---|---|---|---|---|---|---|---|---|---|---|---|---|
| | | 435 | | | | | 440 | | | | | 445 | | | |

| Phe | Thr | Tyr | Lys | Ala | Lys |
|---|---|---|---|---|---|
| | 450 | | | | |

<210> SEQ ID NO 5
<211> LENGTH: 1389
<212> TYPE: DNA
<213> ORGANISM: Acinetobacter calcoaceticus
<220> FEATURE:
<221> NAME/KEY: CDS
<222> LOCATION: (1)..(1389)

<400> SEQUENCE: 5

```
gat gtt cct cta act cca tct caa ttt gct aaa gcg aaa tca gag aac      48
Asp Val Pro Leu Thr Pro Ser Gln Phe Ala Lys Ala Lys Ser Glu Asn
1               5                   10                  15 ttt gac aag aaa gtt att cta tct aat cta aat aag ccg cat gct ttg      96
Phe Asp Lys Lys Val Ile Leu Ser Asn Leu Asn Lys Pro His Ala Leu
            20                  25                  30 tta tgg gga cca gat aat caa att tgg tta act gag cga gca aca ggt     144
Leu Trp Gly Pro Asp Asn Gln Ile Trp Leu Thr Glu Arg Ala Thr Gly
        35                  40                  45 aag att cta aga gtt aat cca gag tcg ggt agt gta aaa aca gtt ttt     192
Lys Ile Leu Arg Val Asn Pro Glu Ser Gly Ser Val Lys Thr Val Phe
    50                  55                  60 cag gta cca gag att gtc aat gat gct gat ggg cag aat ggt tta tta     240
Gln Val Pro Glu Ile Val Asn Asp Ala Asp Gly Gln Asn Gly Leu Leu
65                  70                  75                  80 ggt ttt gcc ttc cat cct gat ttt aaa aat aat cct tat atc tat att     288
Gly Phe Ala Phe His Pro Asp Phe Lys Asn Asn Pro Tyr Ile Tyr Ile
                85                  90                  95 tca ggt aca ttt aaa aat ccg aaa tct aca gat aaa gaa tta ccg aac     336
Ser Gly Thr Phe Lys Asn Pro Lys Ser Thr Asp Lys Glu Leu Pro Asn
            100                 105                 110 caa acg att att cgt cgt tat acc tat aat aaa tca aca gat acg ctc     384
Gln Thr Ile Ile Arg Arg Tyr Thr Tyr Asn Lys Ser Thr Asp Thr Leu
        115                 120                 125 gag aag cca gtc gat tta tta gca gga tta cct tca tca aaa gac cat     432
Glu Lys Pro Val Asp Leu Leu Ala Gly Leu Pro Ser Ser Lys Asp His
    130                 135                 140 cag tca ggt cgt ctt gtc att ggg cca gat caa aag att tat tat acg     480
Gln Ser Gly Arg Leu Val Ile Gly Pro Asp Gln Lys Ile Tyr Tyr Thr
145                 150                 155                 160 att ggt gac caa ggg cgt aac cag ctt gct tat ttg ttc ttg cca aat     528
Ile Gly Asp Gln Gly Arg Asn Gln Leu Ala Tyr Leu Phe Leu Pro Asn
                165                 170                 175 caa gca caa cat acg cca act caa caa gaa ctg aat ggt aaa gac tat     576
Gln Ala Gln His Thr Pro Thr Gln Gln Glu Leu Asn Gly Lys Asp Tyr
            180                 185                 190 cac acc tat atg ggt aaa gta cta cgc tta aat ctt gat gga agt att     624
His Thr Tyr Met Gly Lys Val Leu Arg Leu Asn Leu Asp Gly Ser Ile
        195                 200                 205
```

```
cca aag gat aat cca agt ttt aac ggg gtg gtt agc cat att tat aca      672
Pro Lys Asp Asn Pro Ser Phe Asn Gly Val Val Ser His Ile Tyr Thr
        210                 215                 220 ctt gga cat cgt aat ccg cag ggc tta gca ttc act cca aat ggt aaa      720
Leu Gly His Arg Asn Pro Gln Gly Leu Ala Phe Thr Pro Asn Gly Lys
225                 230                 235                 240 tta ttg cag tct gaa caa ggc cca aac tct gac gat gaa att aac ctc      768
Leu Leu Gln Ser Glu Gln Gly Pro Asn Ser Asp Asp Glu Ile Asn Leu
                245                 250                 255 att gtc aaa ggt ggc aat tat ggt tgg ccg aat gta gca ggt tat aaa      816
Ile Val Lys Gly Gly Asn Tyr Gly Trp Pro Asn Val Ala Gly Tyr Lys
            260                 265                 270 gat gat agt ggc tat gct tat gca aat tat tca gca gca gcc aat aag      864
Asp Asp Ser Gly Tyr Ala Tyr Ala Asn Tyr Ser Ala Ala Ala Asn Lys
        275                 280                 285 tca att aag gat tta gct caa aat gga gta aaa gta gcc gca ggg gtc      912
Ser Ile Lys Asp Leu Ala Gln Asn Gly Val Lys Val Ala Ala Gly Val
    290                 295                 300 cct gtg acg aaa gaa tct gaa tgg act ggt aaa aac ttt gtc cca cca      960
Pro Val Thr Lys Glu Ser Glu Trp Thr Gly Lys Asn Phe Val Pro Pro
305                 310                 315                 320 tta aaa act tta tat acc gtt caa gat acc tac aac tat aac gat cca     1008
Leu Lys Thr Leu Tyr Thr Val Gln Asp Thr Tyr Asn Tyr Asn Asp Pro
                325                 330                 335 act tgt gga gag atg acc tac att tgc tgg cca aca gtt gca ccg tca     1056
Thr Cys Gly Glu Met Thr Tyr Ile Cys Trp Pro Thr Val Ala Pro Ser
            340                 345                 350 tct gcc tat gtc tat aag ggc ggt aaa aaa gca att act ggt tgg gaa     1104
Ser Ala Tyr Val Tyr Lys Gly Gly Lys Lys Ala Ile Thr Gly Trp Glu
        355                 360                 365 aat aca tta ttg gtt cca tct tta aaa cgt ggt gtc att ttc cgt att     1152
Asn Thr Leu Leu Val Pro Ser Leu Lys Arg Gly Val Ile Phe Arg Ile
    370                 375                 380 aag tta gat cca act tat agc act act tat gat gac gct gta ccg atg     1200
Lys Leu Asp Pro Thr Tyr Ser Thr Thr Tyr Asp Asp Ala Val Pro Met
385                 390                 395                 400 ttt aag agc aac aac cgt tat cgt gat gtg att gca agt cca gat ggg     1248
Phe Lys Ser Asn Asn Arg Tyr Arg Asp Val Ile Ala Ser Pro Asp Gly
                405                 410                 415 aat gtc tta tat gta tta act gat act gcc gga tat gtc caa aaa gat     1296
Asn Val Leu Tyr Val Leu Thr Asp Thr Ala Gly Tyr Val Gln Lys Asp
            420                 425                 430 gat ggc tca gta aca aat aca tta gaa aac cca gga tct ctc att aag     1344
Asp Gly Ser Val Thr Asn Thr Leu Glu Asn Pro Gly Ser Leu Ile Lys
        435                 440                 445 ttc acc tat aag gct aag taa tac agt cgc att aaa aaa ccg atc        1389
Phe Thr Tyr Lys Ala Lys     Tyr Ser Arg Ile Lys Lys Pro Ile
    450                 455                 460

<210> SEQ ID NO 6
<211> LENGTH: 454
<212> TYPE: PRT
<213> ORGANISM: Acinetobacter calcoaceticus

<400> SEQUENCE: 6

Asp Val Pro Leu Thr Pro Ser Gln Phe Ala Lys Ala Lys Ser Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
```

```
                  35                  40                  45
Lys Ile Leu Arg Val Asn Pro Glu Ser Gly Ser Val Lys Thr Val Phe
 50                  55                  60

Gln Val Pro Glu Ile Val Asn Asp Ala Asp Gly Gln Asn Gly Leu Leu
 65                  70                  75                  80

Gly Phe Ala Phe His Pro Asp Phe Lys Asn Asn Pro Tyr Ile Tyr Ile
                 85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ser Thr Asp Thr Leu
        115                 120                 125

Glu Lys Pro Val Asp Leu Leu Ala Gly Leu Pro Ser Ser Lys Asp His
130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Ala Asn Lys
        275                 280                 285

Ser Ile Lys Asp Leu Ala Gln Asn Gly Val Lys Val Ala Ala Gly Val
290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
                325                 330                 335

Thr Cys Gly Glu Met Thr Tyr Ile Cys Trp Pro Thr Val Ala Pro Ser
            340                 345                 350

Ser Ala Tyr Val Tyr Lys Gly Gly Lys Lys Ala Ile Thr Gly Trp Glu
        355                 360                 365

Asn Thr Leu Leu Val Pro Ser Leu Lys Arg Gly Val Ile Phe Arg Ile
370                 375                 380

Lys Leu Asp Pro Thr Tyr Ser Thr Thr Tyr Asp Asp Ala Val Pro Met
385                 390                 395                 400

Phe Lys Ser Asn Asn Arg Tyr Arg Asp Val Ile Ala Ser Pro Asp Gly
                405                 410                 415

Asn Val Leu Tyr Val Leu Thr Asp Thr Ala Gly Tyr Val Gln Lys Asp
            420                 425                 430

Asp Gly Ser Val Thr Asn Thr Leu Glu Asn Pro Gly Ser Leu Ile Lys
        435                 440                 445

Phe Thr Tyr Lys Ala Lys
    450
```

-continued

```
<210> SEQ ID NO 7
<211> LENGTH: 1389
<212> TYPE: DNA
<213> ORGANISM: Acinetobacter calcoaceticus
<220> FEATURE:
<221> NAME/KEY: CDS
<222> LOCATION: (1)..(1389)

<400> SEQUENCE: 7 gat gtt cct cta act cca tct caa ttt gct aaa gcg aaa tca gag aac      48
Asp Val Pro Leu Thr Pro Ser Gln Phe Ala Lys Ala Lys Ser Glu Asn
 1               5                  10                  15 ttt gac aag aaa gtt att cta tct aat cta aat aag ccg cat gct ttg      96
Phe Asp Lys Lys Val Ile Leu Ser Asn Leu Asn Lys Pro His Ala Leu
             20                  25                  30 tta tgg gga cca gat aat caa att tgg tta act gag cga gca aca ggt     144
Leu Trp Gly Pro Asp Asn Gln Ile Trp Leu Thr Glu Arg Ala Thr Gly
         35                  40                  45 aag att cta aga gtt aat cca gag tcg ggt agt gta aaa aca gtt ttt     192
Lys Ile Leu Arg Val Asn Pro Glu Ser Gly Ser Val Lys Thr Val Phe
     50                  55                  60 cag gta cca gag att gtc aat gat gct gat ggg cag aat ggt tta tta     240
Gln Val Pro Glu Ile Val Asn Asp Ala Asp Gly Gln Asn Gly Leu Leu
 65                  70                  75                  80 ggt ttt gcc ttc cat cct gat ttt aaa aat aat cct tat atc tat att     288
Gly Phe Ala Phe His Pro Asp Phe Lys Asn Asn Pro Tyr Ile Tyr Ile
                 85                  90                  95 tca ggt aca ttt aaa aat ccg aaa tct aca gat aaa gaa tta ccg aac     336
Ser Gly Thr Phe Lys Asn Pro Lys Ser Thr Asp Lys Glu Leu Pro Asn
            100                 105                 110 caa acg att att cgt cgt tat acc tat aat aaa tca aca gat acg ctc     384
Gln Thr Ile Ile Arg Arg Tyr Thr Tyr Asn Lys Ser Thr Asp Thr Leu
        115                 120                 125 gag aag cca gtc gat tta tta gca gga tta cct tca tca aaa gac cat     432
Glu Lys Pro Val Asp Leu Leu Ala Gly Leu Pro Ser Ser Lys Asp His
    130                 135                 140 cag tca ggt cgt ctt gtc att ggg cca gat caa aag att tat tat acg     480
Gln Ser Gly Arg Leu Val Ile Gly Pro Asp Gln Lys Ile Tyr Tyr Thr
145                 150                 155                 160 att ggt gac caa ggg cgt aac cag ctt gct tat ttg ttc ttg cca aat     528
Ile Gly Asp Gln Gly Arg Asn Gln Leu Ala Tyr Leu Phe Leu Pro Asn
                165                 170                 175 caa gca caa cat acg cca act caa caa gaa ctg aat ggt aaa gac tat     576
Gln Ala Gln His Thr Pro Thr Gln Gln Glu Leu Asn Gly Lys Asp Tyr
            180                 185                 190 cac acc tat atg ggt aaa gta cta cgc tta aat ctt gat gga agt att     624
His Thr Tyr Met Gly Lys Val Leu Arg Leu Asn Leu Asp Gly Ser Ile
        195                 200                 205 cca aag gat aat cca agt ttt aac ggg gtg gtt agc cat att tat aca     672
Pro Lys Asp Asn Pro Ser Phe Asn Gly Val Val Ser His Ile Tyr Thr
    210                 215                 220 ctt gga cat cgt aat ccg cag ggc tta gca ttc act cca aat ggt aaa     720
Leu Gly His Arg Asn Pro Gln Gly Leu Ala Phe Thr Pro Asn Gly Lys
225                 230                 235                 240 tta ttg cag tct gaa caa ggc cca aac tct gac gat gaa att aac ctc     768
Leu Leu Gln Ser Glu Gln Gly Pro Asn Ser Asp Asp Glu Ile Asn Leu
                245                 250                 255 att gtc aaa ggt ggc aat tat ggt tgg ccg aat gta gca ggt tat aaa     816
Ile Val Lys Gly Gly Asn Tyr Gly Trp Pro Asn Val Ala Gly Tyr Lys
            260                 265                 270 gat gat agt ggc tat gct tat gca aat tat tca gca gca gcc aat aag     864
```

```
                                              -continued

Asp Asp Ser Gly Tyr Ala Tyr Ala Asn Tyr Ser Ala Ala Asn Lys
        275                 280                 285 tca att aag gat tta gct caa aat gga gta aaa gta gcc gca ggg gtc       912
Ser Ile Lys Asp Leu Ala Gln Asn Gly Val Lys Val Ala Ala Gly Val
        290                 295                 300 cct gtg acg aaa gaa tct gaa tgg act ggt aaa aac ttt gtc cca cca       960
Pro Val Thr Lys Glu Ser Glu Trp Thr Gly Lys Asn Phe Val Pro Pro
305                 310                 315                 320 tta aaa act tta tat acc gtt caa gat acc tac aac tat aac gat cca      1008
Leu Lys Thr Leu Tyr Thr Val Gln Asp Thr Tyr Asn Tyr Asn Asp Pro
            325                 330                 335 act tgt gga gag atg acc tac att tgc tgg cca aca gtt gca ccg tca      1056
Thr Cys Gly Glu Met Thr Tyr Ile Cys Trp Pro Thr Val Ala Pro Ser
            340                 345                 350 tct gcc tat gtc tat aag ggc ggt aaa aaa gca att act ggt tgg gaa      1104
Ser Ala Tyr Val Tyr Lys Gly Gly Lys Lys Ala Ile Thr Gly Trp Glu
            355                 360                 365 aat aca tta ttg gtt cca tct tta aaa cgt ggt gtc att ttc cgt att      1152
Asn Thr Leu Leu Val Pro Ser Leu Lys Arg Gly Val Ile Phe Arg Ile
370                 375                 380 aag tta gat cca act tat agc act act tat gat gac gct gta ccg atg      1200
Lys Leu Asp Pro Thr Tyr Ser Thr Thr Tyr Asp Asp Ala Val Pro Met
385                 390                 395                 400 ttt aag agc aac aac cgt tat cgt gat gtg att gca agt cca gat ggg      1248
Phe Lys Ser Asn Asn Arg Tyr Arg Asp Val Ile Ala Ser Pro Asp Gly
                405                 410                 415 aat gtc tta tat gta tta act gat act gcc gga gct gtc caa aaa gat      1296
Asn Val Leu Tyr Val Leu Thr Asp Thr Ala Gly Ala Val Gln Lys Asp
            420                 425                 430 gat ggc tca gta aca aat aca tta gaa aac cca gga tct ctc att aag      1344
Asp Gly Ser Val Thr Asn Thr Leu Glu Asn Pro Gly Ser Leu Ile Lys
            435                 440                 445 ttc acc tat aag gct aag taa tac agt cgc att aaa aaa ccg atc          1389
Phe Thr Tyr Lys Ala Lys     Tyr Ser Arg Ile Lys Lys Pro Ile
        450                 455                 460

<210> SEQ ID NO 8
<211> LENGTH: 454
<212> TYPE: PRT
<213> ORGANISM: Acinetobacter calcoaceticus

<400> SEQUENCE: 8

Asp Val Pro Leu Thr Pro Ser Gln Phe Ala Lys Ala Lys Ser Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ser Thr Asp Thr Leu
        115                 120                 125

Glu Lys Pro Val Asp Leu Leu Ala Gly Leu Pro Ser Ser Lys Asp His
```

```
              130                 135                 140
Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Ala Asn Lys
        275                 280                 285

Ser Ile Lys Asp Leu Ala Gln Asn Gly Val Lys Val Ala Ala Gly Val
290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
                325                 330                 335

Thr Cys Gly Glu Met Thr Tyr Ile Cys Trp Pro Thr Val Ala Pro Ser
            340                 345                 350

Ser Ala Tyr Val Tyr Lys Gly Gly Lys Lys Ala Ile Thr Gly Trp Glu
        355                 360                 365

Asn Thr Leu Leu Val Pro Ser Leu Lys Arg Gly Val Ile Phe Arg Ile
370                 375                 380

Lys Leu Asp Pro Thr Tyr Ser Thr Thr Tyr Asp Asp Ala Val Pro Met
385                 390                 395                 400

Phe Lys Ser Asn Asn Arg Tyr Arg Asp Val Ile Ala Ser Pro Asp Gly
                405                 410                 415

Asn Val Leu Tyr Val Leu Thr Asp Thr Ala Gly Ala Val Gln Lys Asp
            420                 425                 430

Asp Gly Ser Val Thr Asn Thr Leu Glu Asn Pro Gly Ser Leu Ile Lys
        435                 440                 445

Phe Thr Tyr Lys Ala Lys
    450

<210> SEQ ID NO 9
<211> LENGTH: 1389
<212> TYPE: DNA
<213> ORGANISM: Acinetobacter calcoaceticus
<220> FEATURE:
<221> NAME/KEY: CDS
<222> LOCATION: (1)..(1389)

<400> SEQUENCE: 9 gat gtt cct cta act cca tct caa ttt gct aaa gcg aaa tca gag aac     48
Asp Val Pro Leu Thr Pro Ser Gln Phe Ala Lys Ala Lys Ser Glu Asn
1               5                   10                  15 ttt gac aag aaa gtt att cta tct aat cta aat aag ccg cat gct ttg     96
Phe Asp Lys Lys Val Ile Leu Ser Asn Leu Asn Lys Pro His Ala Leu
            20                  25                  30
```

| | | |
|---|---|---|
| tta tgg gga cca gat aat caa att tgg tta act gag cga gca aca ggt<br>Leu Trp Gly Pro Asp Asn Gln Ile Trp Leu Thr Glu Arg Ala Thr Gly<br>35                        40                      45 | 144 |
| aag att cta aga gtt aat cca gag tcg ggt agt gta aaa aca gtt ttt<br>Lys Ile Leu Arg Val Asn Pro Glu Ser Gly Ser Val Lys Thr Val Phe<br>    50                      55                      60 | 192 |
| cag gta cca gag att gtc aat gat gct gat ggg cag aat ggt tta tta<br>Gln Val Pro Glu Ile Val Asn Asp Ala Asp Gly Gln Asn Gly Leu Leu<br>65                        70                      75                      80 | 240 |
| ggt ttt gcc ttc cat cct gat ttt aaa aat aat cct tat atc tat att<br>Gly Phe Ala Phe His Pro Asp Phe Lys Asn Asn Pro Tyr Ile Tyr Ile<br>                    85                      90                      95 | 288 |
| tca ggt aca ttt aaa aat ccg aaa tct aca gat aaa gaa tta ccg aac<br>Ser Gly Thr Phe Lys Asn Pro Lys Ser Thr Asp Lys Glu Leu Pro Asn<br>                100                      105                      110 | 336 |
| caa acg att att cgt cgt tat acc tat aat aaa tca aca gat acg ctc<br>Gln Thr Ile Ile Arg Arg Tyr Thr Tyr Asn Lys Ser Thr Asp Thr Leu<br>                115                      120                      125 | 384 |
| gag aag cca gtc gat tta tta gca gga tta cct tca tca aaa gac cat<br>Glu Lys Pro Val Asp Leu Leu Ala Gly Leu Pro Ser Ser Lys Asp His<br>130                        135                      140 | 432 |
| cag tca ggt cgt ctt gtc att ggg cca gat caa aag att tat tat acg<br>Gln Ser Gly Arg Leu Val Ile Gly Pro Asp Gln Lys Ile Tyr Tyr Thr<br>145                    150                      155                      160 | 480 |
| att ggt gac caa ggg cgt aac cag ctt gct tat ttg ttc ttg cca aat<br>Ile Gly Asp Gln Gly Arg Asn Gln Leu Ala Tyr Leu Phe Leu Pro Asn<br>                      165                      170                      175 | 528 |
| caa gca caa cat acg cca act caa caa gaa ctg aat ggt aaa gac tat<br>Gln Ala Gln His Thr Pro Thr Gln Gln Glu Leu Asn Gly Lys Asp Tyr<br>                180                      185                      190 | 576 |
| cac acc tat atg ggt aaa gta cta cgc tta aat ctt gat gga agt att<br>His Thr Tyr Met Gly Lys Val Leu Arg Leu Asn Leu Asp Gly Ser Ile<br>                195                      200                      205 | 624 |
| cca aag gat aat cca agt ttt aac ggg gtg gtt agc cat att tat aca<br>Pro Lys Asp Asn Pro Ser Phe Asn Gly Val Val Ser His Ile Tyr Thr<br>210                        215                      220 | 672 |
| ctt gga cat cgt aat ccg cag ggc tta gca ttc act cca aat ggt aaa<br>Leu Gly His Arg Asn Pro Gln Gly Leu Ala Phe Thr Pro Asn Gly Lys<br>225                        230                      235                      240 | 720 |
| tta ttg cag tct gaa caa ggc cca aac tct gac gat gaa att aac ctc<br>Leu Leu Gln Ser Glu Gln Gly Pro Asn Ser Asp Asp Glu Ile Asn Leu<br>                      245                      250                      255 | 768 |
| att gtc aaa ggt ggc aat tat ggt tgg ccg aat gta gca ggt tat aaa<br>Ile Val Lys Gly Gly Asn Tyr Gly Trp Pro Asn Val Ala Gly Tyr Lys<br>                    260                      265                      270 | 816 |
| gat gat agt ggc tat gct tat gca aat tat tca gca gca gcc aat aag<br>Asp Asp Ser Gly Tyr Ala Tyr Ala Asn Tyr Ser Ala Ala Ala Asn Lys<br>            275                      280                      285 | 864 |
| tca att aag gat tta gct caa aat gga gta aaa gta gcc gca ggg gtc<br>Ser Ile Lys Asp Leu Ala Gln Asn Gly Val Lys Val Ala Ala Gly Val<br>290                        295                      300 | 912 |
| cct gtg acg aaa gaa tct gaa tgg act ggt aaa aac ttt gtc cca cca<br>Pro Val Thr Lys Glu Ser Glu Trp Thr Gly Lys Asn Phe Val Pro Pro<br>305                        310                      315                      320 | 960 |
| tta aaa act tta tat acc gtt caa gat acc tac aac tat aac gat cca<br>Leu Lys Thr Leu Tyr Thr Val Gln Asp Thr Tyr Asn Tyr Asn Asp Pro<br>                      325                      330                      335 | 1008 |
| act tgt gga gag atg acc tac att tgc tgg cca aca gtt gca ccg tca<br>Thr Cys Gly Glu Met Thr Tyr Ile Cys Trp Pro Thr Val Ala Pro Ser<br>                      340                      345                      350 | 1056 |

```
tct gcc tat gtc tat aag ggc ggt aaa aaa gca att act ggt tgg gaa      1104
Ser Ala Tyr Val Tyr Lys Gly Gly Lys Lys Ala Ile Thr Gly Trp Glu
        355                 360                 365 aat aca tta ttg gtt cca tct tta aaa cgt ggt gtc att ttc cgt att      1152
Asn Thr Leu Leu Val Pro Ser Leu Lys Arg Gly Val Ile Phe Arg Ile
370                 375                 380 aag tta gat cca act tat agc act act tat gat gac gct gta ccg atg      1200
Lys Leu Asp Pro Thr Tyr Ser Thr Thr Tyr Asp Asp Ala Val Pro Met
385                 390                 395                 400 ttt aag agc aac aac cgt tat cgt gat gtg att gca agt cca gat ggg      1248
Phe Lys Ser Asn Asn Arg Tyr Arg Asp Val Ile Ala Ser Pro Asp Gly
                405                 410                 415 aat gtc tta tat gta tta act gat act gcc gga aag gtc caa aaa gat      1296
Asn Val Leu Tyr Val Leu Thr Asp Thr Ala Gly Lys Val Gln Lys Asp
            420                 425                 430 gat ggc tca gta aca aat aca tta gaa aac cca gga tct ctc att aag      1344
Asp Gly Ser Val Thr Asn Thr Leu Glu Asn Pro Gly Ser Leu Ile Lys
        435                 440                 445 ttc acc tat aag gct aag taa tac agt cgc att aaa aaa ccg atc          1389
Phe Thr Tyr Lys Ala Lys     Tyr Ser Arg Ile Lys Lys Pro Ile
    450                         455                 460

<210> SEQ ID NO 10
<211> LENGTH: 454
<212> TYPE: PRT
<213> ORGANISM: Acinetobacter calcoaceticus

<400> SEQUENCE: 10

Asp Val Pro Leu Thr Pro Ser Gln Phe Ala Lys Ala Lys Ser Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ser Thr Asp Thr Leu
        115                 120                 125

Glu Lys Pro Val Asp Leu Leu Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
    210                 215                 220

Leu Gly His Arg Asn Pro Gln Gly Leu Ala Phe Thr Pro Asn Gly Lys
```

```
                225                 230                 235                 240
Leu Leu Gln Ser Glu Gln Gly Pro Asn Ser Asp Asp Glu Ile Asn Leu
                    245                 250                 255

Ile Val Lys Gly Gly Asn Tyr Gly Trp Pro Asn Val Ala Gly Tyr Lys
                    260                 265                 270

Asp Asp Ser Gly Tyr Ala Tyr Ala Asn Tyr Ser Ala Ala Asn Lys
                275                 280                 285

Ser Ile Lys Asp Leu Ala Gln Asn Gly Val Lys Val Ala Gly Val
            290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
                    325                 330                 335

Thr Cys Gly Glu Met Thr Tyr Ile Cys Trp Pro Val Ala Pro Ser
                340                 345                 350

Ser Ala Tyr Val Tyr Lys Gly Gly Lys Ala Ile Thr Gly Trp Glu
                355                 360                 365

Asn Thr Leu Leu Val Pro Ser Leu Lys Arg Gly Val Ile Phe Arg Ile
    370                 375                 380

Lys Leu Asp Pro Thr Tyr Ser Thr Thr Tyr Asp Asp Ala Val Pro Met
385                 390                 395                 400

Phe Lys Ser Asn Asn Arg Tyr Arg Asp Val Ile Ala Ser Pro Asp Gly
                    405                 410                 415

Asn Val Leu Tyr Val Leu Thr Asp Thr Ala Gly Lys Val Gln Lys Asp
                420                 425                 430

Asp Gly Ser Val Thr Asn Thr Leu Glu Asn Pro Gly Ser Leu Ile Lys
            435                 440                 445

Phe Thr Tyr Lys Ala Lys
        450

<210> SEQ ID NO 11
<211> LENGTH: 1389
<212> TYPE: DNA
<213> ORGANISM: Acinetobacter calcoaceticus
<220> FEATURE:
<221> NAME/KEY: CDS
<222> LOCATION: (1)..(1389)

<400> SEQUENCE: 11 gat gtt cct cta act cca tct caa ttt gct aaa gcg aaa tca gag aac    48
Asp Val Pro Leu Thr Pro Ser Gln Phe Ala Lys Ala Lys Ser Glu Asn
1               5                   10                  15 ttt gac aag aaa gtt att cta tct aat cta aat aag ccg cat gct ttg    96
Phe Asp Lys Lys Val Ile Leu Ser Asn Leu Asn Lys Pro His Ala Leu
            20                  25                  30 tta tgg gga cca gat aat caa att tgg tta act gag cga gca aca ggt   144
Leu Trp Gly Pro Asp Asn Gln Ile Trp Leu Thr Glu Arg Ala Thr Gly
        35                  40                  45 aag att cta aga gtt aat cca gag tcg ggt agt gta aaa aca gtt ttt   192
Lys Ile Leu Arg Val Asn Pro Glu Ser Gly Ser Val Lys Thr Val Phe
    50                  55                  60 cag gta cca gag att gtc aat gat gct gat ggg cag aat ggt tta tta   240
Gln Val Pro Glu Ile Val Asn Asp Ala Asp Gly Gln Asn Gly Leu Leu
65                  70                  75                  80 ggt ttt gcc ttc cat cct gat ttt aaa aat aat cct tat atc tat att   288
Gly Phe Ala Phe His Pro Asp Phe Lys Asn Asn Pro Tyr Ile Tyr Ile
                85                  90                  95 tca ggt aca ttt aaa aat ccg aaa tct aca gat aaa gaa tta ccg aac   336
```

```
              Ser Gly Thr Phe Lys Asn Pro Lys Ser Thr Asp Lys Glu Leu Pro Asn
                          100                 105                 110 caa acg att att cgt cgt tat acc tat aat aaa tca aca gat acg ctc        384
Gln Thr Ile Ile Arg Arg Tyr Thr Tyr Asn Lys Ser Thr Asp Thr Leu
            115                 120                 125 gag aag cca gtc gat tta tta gca gga tta cct tca tca aaa gac cat        432
Glu Lys Pro Val Asp Leu Leu Ala Gly Leu Pro Ser Ser Lys Asp His
        130                 135                 140 cag tca ggt cgt ctt gtc att ggg cca gat caa aag att tat tat acg        480
Gln Ser Gly Arg Leu Val Ile Gly Pro Asp Gln Lys Ile Tyr Tyr Thr
145                 150                 155                 160 att ggt gac caa ggg cgt aac cag ctt gct tat ttg ttc ttg cca aat        528
Ile Gly Asp Gln Gly Arg Asn Gln Leu Ala Tyr Leu Phe Leu Pro Asn
                165                 170                 175 caa gca caa cat acg cca act caa caa gaa ctg aat ggt aaa gac tat        576
Gln Ala Gln His Thr Pro Thr Gln Gln Glu Leu Asn Gly Lys Asp Tyr
            180                 185                 190 cac acc tat atg ggt aaa gta cta cgc tta aat ctt gat gga agt att        624
His Thr Tyr Met Gly Lys Val Leu Arg Leu Asn Leu Asp Gly Ser Ile
        195                 200                 205 cca aag gat aat cca agt ttt aac ggg gtg gtt agc cat att tat aca        672
Pro Lys Asp Asn Pro Ser Phe Asn Gly Val Val Ser His Ile Tyr Thr
    210                 215                 220 ctt gga cat cgt aat ccg cag ggc tta gca ttc act cca aat ggt aaa        720
Leu Gly His Arg Asn Pro Gln Gly Leu Ala Phe Thr Pro Asn Gly Lys
225                 230                 235                 240 tta ttg cag tct gaa caa ggc cca aac tct gac gat gaa att aac ctc        768
Leu Leu Gln Ser Glu Gln Gly Pro Asn Ser Asp Asp Glu Ile Asn Leu
                245                 250                 255 att gtc aaa ggt ggc aat tat ggt tgg ccg aat gta gca ggt tat aaa        816
Ile Val Lys Gly Gly Asn Tyr Gly Trp Pro Asn Val Ala Gly Tyr Lys
            260                 265                 270 gat gat agt ggc tat gct tat gca aat tat tca gca gca gcc aat aag        864
Asp Asp Ser Gly Tyr Ala Tyr Ala Asn Tyr Ser Ala Ala Ala Asn Lys
        275                 280                 285 tca att aag gat tta gct caa aat gga gta aaa gta gcc gca ggg gtc        912
Ser Ile Lys Asp Leu Ala Gln Asn Gly Val Lys Val Ala Ala Gly Val
    290                 295                 300 cct gtg acg aaa gaa tct gaa tgg act ggt aaa aac ttt gtc cca cca        960
Pro Val Thr Lys Glu Ser Glu Trp Thr Gly Lys Asn Phe Val Pro Pro
305                 310                 315                 320 tta aaa act tta tat acc gtt caa gat acc tac aac tat aac gat cca        1008
Leu Lys Thr Leu Tyr Thr Val Gln Asp Thr Tyr Asn Tyr Asn Asp Pro
                325                 330                 335 act tgt gga gag atg acc tac att tgc tgg cca aca gtt gca ccg tca        1056
Thr Cys Gly Glu Met Thr Tyr Ile Cys Trp Pro Thr Val Ala Pro Ser
            340                 345                 350 tct gcc tat gtc tat aag ggc ggt aaa aaa gca att act ggt tgg gaa        1104
Ser Ala Tyr Val Tyr Lys Gly Gly Lys Lys Ala Ile Thr Gly Trp Glu
        355                 360                 365 aat aca tta ttg gtt cca tct tta aaa cgt ggt gtc att ttc cgt att        1152
Asn Thr Leu Leu Val Pro Ser Leu Lys Arg Gly Val Ile Phe Arg Ile
    370                 375                 380 aag tta gat cca act tat agc act act tat gat gac gct gta ccg atg        1200
Lys Leu Asp Pro Thr Tyr Ser Thr Thr Tyr Asp Asp Ala Val Pro Met
385                 390                 395                 400 ttt aag agc aac aac cgt tat cgt gat gtg att gca agt cca gat ggg        1248
Phe Lys Ser Asn Asn Arg Tyr Arg Asp Val Ile Ala Ser Pro Asp Gly
                405                 410                 415 aat gtc tta tat gta tta act gat act gcc gga gac gtc caa aaa gat        1296
```

```
Asn Val Leu Tyr Val Leu Thr Asp Thr Ala Gly Asp Val Gln Lys Asp
                420                 425                 430 gat ggc tca gta aca aat aca tta gaa aac cca gga tct ctc att aag      1344
Asp Gly Ser Val Thr Asn Thr Leu Glu Asn Pro Gly Ser Leu Ile Lys
        435                 440                 445 ttc acc tat aag gct aag taa tac agt cgc att aaa aaa ccg atc          1389
Phe Thr Tyr Lys Ala Lys     Tyr Ser Arg Ile Lys Lys Pro Ile
450                 455                 460
```

<210> SEQ ID NO 12
<211> LENGTH: 454
<212> TYPE: PRT
<213> ORGANISM: Acinetobacter calcoaceticus

<400> SEQUENCE: 12

```
Asp Val Pro Leu Thr Pro Ser Gln Phe Ala Lys Ala Lys Ser Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
        35                  40                  45

Lys Ile Leu Arg Val Asn Pro Glu Ser Gly Ser Val Lys Thr Val Phe
    50                  55                  60

Gln Val Pro Glu Ile Val Asn Asp Ala Asp Gly Gln Asn Gly Leu Leu
65                  70                  75                  80

Gly Phe Ala Phe His Pro Asp Phe Lys Asn Asn Pro Tyr Ile Tyr Ile
                85                  90                  95

Ser Gly Thr Phe Lys Asn Pro Lys Ser Thr Asp Lys Glu Leu Pro Asn
            100                 105                 110

Gln Thr Ile Ile Arg Arg Tyr Thr Tyr Asn Lys Ser Thr Asp Thr Leu
        115                 120                 125

Glu Lys Pro Val Asp Leu Leu Ala Gly Leu Pro Ser Ser Lys Asp His
    130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Gly Lys Asp Tyr
            180                 185                 190

His Thr Tyr Met Gly Lys Val Leu Arg Leu Asn Leu Asp Gly Ser Ile
        195                 200                 205

Pro Lys Asp Asn Pro Ser Phe Asn Gly Val Val Ser His Ile Tyr Thr
    210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
            260                 265                 270

Asp Asp Ser Gly Tyr Ala Tyr Ala Asn Tyr Ser Ala Ala Ala Asn Lys
        275                 280                 285

Ser Ile Lys Asp Leu Ala Gln Asn Gly Val Lys Val Ala Ala Gly Val
    290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
```

```
                               325                 330                 335
Thr Cys Gly Glu Met Thr Tyr Ile Cys Trp Pro Thr Val Ala Pro Ser
            340                 345                 350

Ser Ala Tyr Val Tyr Lys Gly Gly Lys Lys Ala Ile Thr Gly Trp Glu
        355                 360                 365

Asn Thr Leu Leu Val Pro Ser Leu Lys Arg Gly Val Ile Phe Arg Ile
    370                 375                 380

Lys Leu Asp Pro Thr Tyr Ser Thr Tyr Asp Asp Ala Val Pro Met
385                 390                 395                 400

Phe Lys Ser Asn Asn Arg Tyr Arg Asp Val Ile Ala Ser Pro Asp Gly
                405                 410                 415

Asn Val Leu Tyr Val Leu Thr Asp Thr Ala Gly Asp Val Gln Lys Asp
            420                 425                 430

Asp Gly Ser Val Thr Asn Thr Leu Glu Asn Pro Gly Ser Leu Ile Lys
        435                 440                 445

Phe Thr Tyr Lys Ala Lys
    450

<210> SEQ ID NO 13
<211> LENGTH: 1389
<212> TYPE: DNA
<213> ORGANISM: Acinetobacter calcoaceticus
<220> FEATURE:
<221> NAME/KEY: CDS
<222> LOCATION: (1)..(1389)

<400> SEQUENCE: 13 gat gtt cct cta act cca tct caa ttt gct aaa gcg aaa tca gag aac        48
Asp Val Pro Leu Thr Pro Ser Gln Phe Ala Lys Ala Lys Ser Glu Asn
1               5                   10                  15 ttt gac aag aaa gtt att cta tct aat cta aat aag ccg cat gct ttg        96
Phe Asp Lys Lys Val Ile Leu Ser Asn Leu Asn Lys Pro His Ala Leu
            20                  25                  30 tta tgg gga cca gat aat caa att tgg tta act gag cga gca aca ggt       144
Leu Trp Gly Pro Asp Asn Gln Ile Trp Leu Thr Glu Arg Ala Thr Gly
        35                  40                  45 aag att cta aga gtt aat cca gag tcg ggt agt gta aaa aca gtt ttt       192
Lys Ile Leu Arg Val Asn Pro Glu Ser Gly Ser Val Lys Thr Val Phe
    50                  55                  60 cag gta cca gag att gtc aat gat gct gat ggg cag aat ggt tta tta       240
Gln Val Pro Glu Ile Val Asn Asp Ala Asp Gly Gln Asn Gly Leu Leu
65                  70                  75                  80 ggt ttt gcc ttc cat cct gat ttt aaa aat aat cct tat atc tat att       288
Gly Phe Ala Phe His Pro Asp Phe Lys Asn Asn Pro Tyr Ile Tyr Ile
                85                  90                  95 tca ggt aca ttt aaa aat ccg aaa tct aca gat aaa gaa tta ccg aac       336
Ser Gly Thr Phe Lys Asn Pro Lys Ser Thr Asp Lys Glu Leu Pro Asn
            100                 105                 110 caa acg att att cgt cgt tat acc tat aat aaa tca aca gat acg ctc       384
Gln Thr Ile Ile Arg Arg Tyr Thr Tyr Asn Lys Ser Thr Asp Thr Leu
        115                 120                 125 gag aag cca gtc gat tta tta gca gga tta cct tca tca aaa gac cat       432
Glu Lys Pro Val Asp Leu Leu Ala Gly Leu Pro Ser Ser Lys Asp His
    130                 135                 140 cag tca ggt cgt ctt gtc att ggg cca gat caa aag att tat tat acg       480
Gln Ser Gly Arg Leu Val Ile Gly Pro Asp Gln Lys Ile Tyr Tyr Thr
145                 150                 155                 160 att ggt gac caa ggg cgt aac cag ctt gct tat ttg ttc ttg cca aat       528
Ile Gly Asp Gln Gly Arg Asn Gln Leu Ala Tyr Leu Phe Leu Pro Asn
                165                 170                 175
```

```
caa gca caa cat acg cca act caa caa gaa ctg aat ggt aaa gac tat      576
Gln Ala Gln His Thr Pro Thr Gln Gln Glu Leu Asn Gly Lys Asp Tyr
            180                 185                 190 cac acc tat atg ggt aaa gta cta cgc tta aat ctt gat gga agt att      624
His Thr Tyr Met Gly Lys Val Leu Arg Leu Asn Leu Asp Gly Ser Ile
        195                 200                 205 cca aag gat aat cca agt ttt aac ggg gtg gtt agc cat att tat aca      672
Pro Lys Asp Asn Pro Ser Phe Asn Gly Val Val Ser His Ile Tyr Thr
    210                 215                 220 ctt gga cat cgt aat ccg cag ggc tta gca ttc act cca aat ggt aaa      720
Leu Gly His Arg Asn Pro Gln Gly Leu Ala Phe Thr Pro Asn Gly Lys
225                 230                 235                 240 tta ttg cag tct gaa caa ggc cca aac tct gac gat gaa att aac ctc      768
Leu Leu Gln Ser Glu Gln Gly Pro Asn Ser Asp Asp Glu Ile Asn Leu
                245                 250                 255 att gtc aaa ggt ggc aat tat ggt tgg ccg aat gta gca ggt tat aaa      816
Ile Val Lys Gly Gly Asn Tyr Gly Trp Pro Asn Val Ala Gly Tyr Lys
            260                 265                 270 gat gat agt ggc tat gct tat gca aat tat tca gca gca gcc aat aag      864
Asp Asp Ser Gly Tyr Ala Tyr Ala Asn Tyr Ser Ala Ala Ala Asn Lys
        275                 280                 285 tca att aag gat tta gct caa aat gga gta aaa gta gcc gca ggg gtc      912
Ser Ile Lys Asp Leu Ala Gln Asn Gly Val Lys Val Ala Ala Gly Val
    290                 295                 300 cct gtg acg aaa gaa tct gaa tgg act ggt aaa aac ttt gtc cca cca      960
Pro Val Thr Lys Glu Ser Glu Trp Thr Gly Lys Asn Phe Val Pro Pro
305                 310                 315                 320 tta aaa act tta tat acc gtt caa gat acc tac aac tat aac gat cca     1008
Leu Lys Thr Leu Tyr Thr Val Gln Asp Thr Tyr Asn Tyr Asn Asp Pro
                325                 330                 335 act tgt gga gag atg acc tac att tgc tgg cca aca gtt gca ccg tca     1056
Thr Cys Gly Glu Met Thr Tyr Ile Cys Trp Pro Thr Val Ala Pro Ser
            340                 345                 350 tct gcc tat gtc tat aag ggc ggt aaa aaa gca att act ggt tgg gaa     1104
Ser Ala Tyr Val Tyr Lys Gly Gly Lys Lys Ala Ile Thr Gly Trp Glu
        355                 360                 365 aat aca tta ttg gtt cca tct tta aaa cgt ggt gtc att ttc cgt att     1152
Asn Thr Leu Leu Val Pro Ser Leu Lys Arg Gly Val Ile Phe Arg Ile
    370                 375                 380 aag tta gat cca act tat agc act act tat gat gac gct gta ccg atg     1200
Lys Leu Asp Pro Thr Tyr Ser Thr Thr Tyr Asp Asp Ala Val Pro Met
385                 390                 395                 400 ttt aag agc aac aac cgt tat cgt gat gtg att gca agt cca gat ggg     1248
Phe Lys Ser Asn Asn Arg Tyr Arg Asp Val Ile Ala Ser Pro Asp Gly
                405                 410                 415 aat gtc tta tat gta tta act gat act gcc gga gaa gtc caa aaa gat     1296
Asn Val Leu Tyr Val Leu Thr Asp Thr Ala Gly Glu Val Gln Lys Asp
            420                 425                 430 gat ggc tca gta aca aat aca tta gaa aac cca gga tct ctc att aag     1344
Asp Gly Ser Val Thr Asn Thr Leu Glu Asn Pro Gly Ser Leu Ile Lys
        435                 440                 445 ttc acc tat aag gct aag taa tac agt cgc att aaa aaa ccg atc         1389
Phe Thr Tyr Lys Ala Lys     Tyr Ser Arg Ile Lys Lys Pro Ile
    450                         455                 460

<210> SEQ ID NO 14
<211> LENGTH: 454
<212> TYPE: PRT
<213> ORGANISM: Acinetobacter calcoaceticus

<400> SEQUENCE: 14
```

```
Asp Val Pro Leu Thr Pro Ser Gln Phe Ala Lys Ala Lys Ser Glu Asn
1               5                   10                  15

Phe Asp Lys Lys Val Ile Leu Ser Asn Leu Asn Lys Pro His Ala Leu
            20                  25                  30

Leu Trp Gly Pro Asp Asn Gln Ile Trp Leu Thr Glu Arg Ala Thr Gly
            35                  40                  45

Lys Ile Leu Arg Val Asn Pro Glu Ser Gly Ser Val Lys Thr Val Phe
50                      55                  60

Gln Val Pro Glu Ile Val Asn Asp Ala Asp Gly Gln Asn Gly Leu Leu
65                      70                  75                  80

Gly Phe Ala Phe His Pro Asp Phe Lys Asn Asn Pro Tyr Ile Tyr Ile
                85                  90                  95

Ser Gly Thr Phe Lys Asn Pro Lys Ser Thr Asp Lys Glu Leu Pro Asn
                100                 105                 110

Gln Thr Ile Ile Arg Arg Tyr Thr Tyr Asn Lys Ser Thr Asp Thr Leu
                115                 120                 125

Glu Lys Pro Val Asp Leu Leu Ala Gly Leu Pro Ser Ser Lys Asp His
            130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                165                 170                 175

Gln Ala Gln His Thr Pro Thr Gln Gln Glu Leu Asn Gly Lys Asp Tyr
                180                 185                 190

His Thr Tyr Met Gly Lys Val Leu Arg Leu Asn Leu Asp Gly Ser Ile
            195                 200                 205

Pro Lys Asp Asn Pro Ser Phe Asn Gly Val Val Ser His Ile Tyr Thr
            210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                245                 250                 255

Ile Val Lys Gly Gly Asn Tyr Gly Trp Pro Asn Val Ala Gly Tyr Lys
                260                 265                 270

Asp Asp Ser Gly Tyr Ala Tyr Ala Asn Tyr Ser Ala Ala Ala Asn Lys
            275                 280                 285

Ser Ile Lys Asp Leu Ala Gln Asn Gly Val Lys Val Ala Ala Gly Val
            290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
                325                 330                 335

Thr Cys Gly Glu Met Thr Tyr Ile Cys Trp Pro Thr Val Ala Pro Ser
            340                 345                 350

Ser Ala Tyr Val Tyr Lys Gly Gly Lys Lys Ala Ile Thr Gly Trp Glu
                355                 360                 365

Asn Thr Leu Leu Val Pro Ser Leu Lys Arg Gly Val Ile Phe Arg Ile
            370                 375                 380

Lys Leu Asp Pro Thr Tyr Ser Thr Thr Tyr Asp Asp Ala Val Pro Met
385                 390                 395                 400

Phe Lys Ser Asn Asn Arg Tyr Arg Asp Val Ile Ala Ser Pro Asp Gly
                405                 410                 415

Asn Val Leu Tyr Val Leu Thr Asp Thr Ala Gly Glu Val Gln Lys Asp
```

```
                420               425               430
Asp Gly Ser Val Thr Asn Thr Leu Glu Asn Pro Gly Ser Leu Ile Lys
        435                 440                 445

Phe Thr Tyr Lys Ala Lys
    450

<210> SEQ ID NO 15
<211> LENGTH: 27
<212> TYPE: DNA
<213> ORGANISM: Acinetobacter calcoaceticus

<400> SEQUENCE: 15
gatactgccg gagctgtcca aaaagat                                          27

<210> SEQ ID NO 16
<211> LENGTH: 27
<212> TYPE: DNA
<213> ORGANISM: Acinetobacter calcoaceticus

<400> SEQUENCE: 16 atcttttttgg acagctccgg cagtatc                                         27

<210> SEQ ID NO 17
<211> LENGTH: 27
<212> TYPE: DNA
<213> ORGANISM: Acinetobacter calcoaceticus

<400> SEQUENCE: 17
gatactgccg gaaaggtcca aaaagat                                          27

<210> SEQ ID NO 18
<211> LENGTH: 27
<212> TYPE: DNA
<213> ORGANISM: Acinetobacter calcoaceticus

<400> SEQUENCE: 18 atcttttttgg acctttccgg cagtatc                                         27

<210> SEQ ID NO 19
<211> LENGTH: 27
<212> TYPE: DNA
<213> ORGANISM: Acinetobacter calcoaceticus

<400> SEQUENCE: 19
gatactgccg gatatgtcca aaaagat                                          27

<210> SEQ ID NO 20
<211> LENGTH: 27
<212> TYPE: DNA
<213> ORGANISM: Acinetobacter calcoaceticus

<400> SEQUENCE: 20 atcttttttgg acatatccgg cagtatc                                         27

<210> SEQ ID NO 21
<211> LENGTH: 27
<212> TYPE: DNA
<213> ORGANISM: Acinetobacter calcoaceticus

<400> SEQUENCE: 21
gatactgccg gagacgtcca aaaagat                                          27

<210> SEQ ID NO 22
```

```
<211> LENGTH: 27
<212> TYPE: DNA
<213> ORGANISM: Acinetobacter calcoaceticus

<400> SEQUENCE: 22
atcttttggg acgtctccgg cagtatc                                              27

<210> SEQ ID NO 23
<211> LENGTH: 27
<212> TYPE: DNA
<213> ORGANISM: Acinetobacter calcoaceticus

<400> SEQUENCE: 23
gatactgccg gagaagtcca aaaagat                                              27

<210> SEQ ID NO 24
<211> LENGTH: 27
<212> TYPE: DNA
<213> ORGANISM: Acinetobacter calcoaceticus

<400> SEQUENCE: 24
atcttttggg acttctccgg cagtatc                                              27

<210> SEQ ID NO 25
<211> LENGTH: 27
<212> TYPE: DNA
<213> ORGANISM: Acinetobacter calcoaceticus

<400> SEQUENCE: 25
gatactgccg gatgtgtcca aaaagat                                              27

<210> SEQ ID NO 26
<211> LENGTH: 27
<212> TYPE: DNA
<213> ORGANISM: Acinetobacter calcoaceticus

<400> SEQUENCE: 26
atcttttggg acacatccgg cagtatc                                              27
```

MUTANTS OF PYRROLOQUINOLINE QUININE-DEPENDENT SOLUBLE GLUCOSE DEHYDROGENASE

The present invention relates to the field of the development of glucose electrodes that are of interest in glucose assay, in particular of blood glucose of diabetic subjects, and for the application of biofuel cells using glucose as fuel.

The present invention relates more particularly to mutants of the enzyme pyrroloquinoline-quinone soluble glucose dehydrogenase (also called PQQ s-GDH) which have advantageous properties relative to the wild-type enzyme.

Type 2 diabetes affects nearly two million people in France, to which we must add 600 000 who are unaware of their disease. In the United States the situation is even more critical. In the developed countries, diabetes is the main cause of blindness in the age range 20-65 years.

Monitoring and management of the disease are based on, among other things, daily determination of blood glucose and injection of insulin. Various companies offer glucose sensors that enable patients to measure their blood sugar level themselves. These sensors can be amperometric, potentiometric or coulometric; they are all based on the use of an enzyme capable of oxidizing glucose; the two principal enzymes being glucose oxidase and PQQ s-GDH.

The pyrroloquinoline quinone glucose dehydrogenases belong to the family of quinoproteins, which have been identified in *Acinetobacter calcoaceticus*; there are two types: one is a membrane enzyme and the other is a soluble enzyme. They catalyze the oxidation of glucose to D-gluconolactone and can be used as a supplier of electrons.

The PQQ s-GDH of *Acinetobacter calcoaceticus* is composed of a homodimer consisting of two subunits of about 50 kDa (apoenzyme) and a pyrroloquinoline quinone cofactor (PQQ) (Oubrié et al., J. Mol. Biol; 289, 319-333 (1999)). This enzyme has an active site, within which the oxidation of glucose is catalyzed in the presence of PQQ; this active site is composed of the amino acids located at positions 76, 144, 169, 343, 346 and 428.

PQQ s-GDH is of considerable industrial interest as it is easily obtainable in large amounts; it has thus become the main enzyme used in glucose sensors for self-monitoring of blood sugar level. The advantage of the quinoproteins is that they are not dependent on oxygen, in contrast to glucose oxidase which utilizes $O_2$ as electron acceptor.

Based on its physicochemical properties, it is also conceivable to use PQQ s-GDH for making biofuel cells, the principle of which is based on the oxidation of glucose to produce an electric current.

The drawback of PQQ s-GDH is its low thermal stability, its low stability at physiological pH and its moderate activity.

Several authors have tried to develop variants of PQQ s-GDH in order to improve its properties.

"Mutant" or "variant" means a PQQ s-GDH whose protein sequence comprises the insertion, deletion and/or substitution of at least one amino acid relative to the protein sequence of the wild-type PQQ s-GDH; hereinafter, the reference nucleotide and protein sequences of PQQ s-GDH are those of the wild-type PQQ s-GDH of *Acinetobacter calcoaceticus* (respectively SEQ. ID. No. 1 and 2).

Mutations Aiming to Improve the Stability of PQQ s-GDH

U.S. Pat. No. 7,244,600 describes a PQQ s-GDH mutated in such a way that the two subunits are joined together by a disulfide bridge. The mutation consists of replacing at least one amino acid at positions 415 and 414 and/or simultaneously the two amino acids located at positions 340 and 418 with a cysteine residue. These modifications endow the enzyme with better thermal stability.

Mutation Aiming to Make PQQ s-GDH Less Sensitive to Inhibition by its Substrate

U.S. Pat. No. 7,244,581 describes a PQQ s-GDH in which at least one amino acid in the region 349-377 is replaced with a different amino acid. This modification leads to an enzyme which is less sensitive to inhibition by the substrate and can thus be used in the presence of high concentrations of glucose.

Mutations Aiming to Make PQQ s-GDH More Specific to its Natural Substrate (Glucose)

It is also possible to modify the wild-type PQQ s-GDH to make it more substrate-specific. An enzyme that is specific to a substrate will only catalyze the reaction involving said substrate, and conversely, an enzyme with low substrate specificity is able to catalyze reactions based on substrates structurally similar to the natural substrate. The natural substrate of PQQ s-GDH is glucose but the wild-type PQQ s-GDH has low specificity and is also able to catalyze the oxidation of other monosaccharides, and disaccharides.

Several authors have proposed modifying the wild-type PQQ s-GDH in order to make it more specific to glucose:
  thus, patent application US 2007/0105173 proposes modifying PQQ s-GDH by substituting at least one of the amino acids located at positions 49, 67 to 69, 76, 89, 129 to 131, 167 to 170, 174, 188, 189, 207, 215, 245, 249, 300, 341 to 343, 349, 351 and 429 and/or by introducing an amino acid between positions 428 and 429;
  patent application EP 1 367 120 proposes modifying PQQ s-GDH by inserting a leucine, a lysine or an alanine between positions 428 and 429;
  U.S. Pat. No. 7,037,698 describes a substitution of the amino acid at one of the positions 75, 326 to 354, 278 to 320 and 162 to 197 of PQQ s-GDH;
  patent application US 2007/0243566 recommends inserting an amino acid between positions 428 and 429 and, optionally, substituting the amino acid at position 428 with a leucine, proline or valine of PQQ s-GDH;
  international application WO 2006/085509 describes mutants of the PQQ s-GDH of *Acinetobacter* having one or more substitutions at positions 125, 128, 142, 168, 169, 170, 224, 230, 236, 345, 351, 416 or 428; this document then lists specific mutants having numerous mutated sites;
  patent application EP 1 666 586 cites mutants of the PQQ s-GDH of *Acinetobacter baumanii* bearing the insertion of a leucine, an alanine or a lysine between positions 428 and 429 or mutants for which the amino acid of position 429 is substituted with a phenylalanine, a proline, a leucine or a tyrosine;
  U.S. Pat. No. 7,132,270 proposes substituting the amino acids of position 348 with an alanine, a glycine or a serine and of position 428 with a leucine, a proline or a valine.

For use in glucose sensors, it is necessary to have PQQ s-GDH mutants that are more active, i.e. which permit a faster reaction of transformation of glucose to D-gluconolactone, which is not possible with the existing mutants.

It is thus still necessary to develop a PQQ s-GDH that would display better activity than the wild-type PQQ s-GDH while retaining satisfactory or even improved thermal and pH stability.

To meet this need, the inventors have developed novel mutants of the wild-type PQQ s-GDH of *Acinetobacter calcoaceticus*; these mutants are such that the asparagine located at position 428 is substituted with a cysteine, a tyrosine, an alanine, an aspartate or a glutamate.

Thus, a first object of the invention relates to a PQQ s-GDH mutant having a percentage identity of at least 80% relative to the wild-type PQQ s-GDH of *Acinetobacter calcoaceticus*, characterized in that its amino acid located at position 428, referring to the protein sequence of the wild-type PQQ s-GDH of *Acinetobacter calcoaceticus* (SEQ. ID. No. 2), is substituted with an amino acid selected from the group comprising a cysteine, a tyrosine, an alanine, an aspartate or a glutamate.

During the research that led to the present invention, the inventors also prepared a PQQ s-GDH mutant characterized in that its amino acid located at position 428, referring to the protein sequence of the wild-type PQQ s-GDH of *Acinetobacter calcoaceticus* (SEQ. ID. No. 2), is substituted with a lysine o (see examples, part 4); this mutant has the protein sequence SEQ. ID. No. 10 and is encoded by the nucleic acid molecule of SEQ. ID. No. 9. This mutant can be prepared with the oligonucleotides of SEQ. ID. No. 17 and 18 presented in Table I below.

The numbering of the amino acids refers to the sequence of the wild-type PQQ s-GDH of *Acinetobacter calcoaceticus*; the PQQ s-GDH mutants according to the present invention are not, however, limited to the mutants of the wild-type PQQ s-GDH of *Acinetobacter calcoaceticus*, the present invention also relates to the mutants of PQQ s-GDH having a percentage identity of at least 90% relative to the wild-type PQQ s-GDH of *Acinetobacter calcoaceticus*.

The identity of a sequence relative to the sequence of the wild-type PQQ s-GDH of *Acinetobacter calcoaceticus* (SEQ. ID. No. 2) as reference sequence is evaluated as a function of the percentage of amino acid residues that are identical, when the two sequences are aligned, so as to obtain maximum correspondence between them.

The percentage identity can be calculated by a person skilled in the art using a computer program for comparing sequences, such as for example that of the BLAST suite (Altschul et al., NAR, 25, 3389-3402). The BLAST programs are employed on the comparison window consisting of the whole of SEQ. ID. No. 2 indicated as reference sequence.

A peptide having an amino acid sequence having at least X % of identity with a reference sequence is defined, in the present invention, as a peptide whose sequence can include up to 100-X alterations for 100 amino acids of the reference sequence, while preserving the functional properties of said reference peptide, in the present case its enzyme activity of oxidation of glucose. In the sense of the present invention, the term alteration includes deletions, substitutions or consecutive or dispersed insertions of amino acids in the reference sequence.

The amino acid corresponding to the amino acid located at position 428 of the PQQ s-GDH of *Acinetobacter calcoaceticus* is identified by alignment of the sequence of said homologous enzyme with the PQQ s-GDH of *Acinetobacter calcoaceticus*.

The invention relates in particular to a PQQ s-GDH mutant having an amino acid sequence selected from SEQ. ID. No. 4, 6, 8, 12 and 14, corresponding respectively to the amino acid sequences of cysteine, tyrosine, alanine, aspartate and glutamate mutants of PQQ s-GDH; these mutated enzymes are encoded by nucleotide fragments obtained by mutation of the gene of the PQQ s-GDH of *Acinetobacter calcoaceticus* with suitable pairs of oligonucleotides.

These novel PQQ s-GDH mutants according to the invention display improved performance relative to the wild-type enzyme of *Acinetobacter calcoaceticus*, which is the enzyme used in the commercially available glucose sensors:

their activity is greater than that of the wild-type enzyme, especially at physiological concentrations of glucose, i.e. between 1 and 10 mM;

The activity of the enzyme can be quantified by monitoring the coloration of redox reagents occurring during the reaction of oxidation of glucose to gluconolactone by PQQ s-GDH; the redox reagents are for example phenazine methosulfate (PMS) in combination with 2,6-dichlorophenolindophenol (DCIP), potassium ferricyanide, and ferrocene.

they are less sensitive to the inhibitory effect of glucose at high concentration.

The specificity of a PQQ s-GDH mutant for a substrate can be evaluated by comparing the enzyme activity of said mutant on glucose and on several other sugars such as disaccharides as substrate.

The advantageous properties of the PQQ s-GDH mutants according to the invention make their use particularly suitable for bioelectric systems such as biofuel cells using glucose as the source of energy and glucose biosensors.

The present invention also relates to a nucleic acid molecule coding for a PQQ s-GDH mutant according to the invention; said nucleic acid molecule being obtained by modifying a wild-type PQQ s-GDH, such as that of *Acinetobacter calcoaceticus*, with a pair of oligonucleotides selected from the group consisting of the pairs of oligonucleotides shown in Table I.

TABLE I list and sequence of the oligonucleotides used for preparing the PQQ s-GDH mutants according to the invention.

| Oligonucleotides | sequences |
|---|---|
| Pair of oligonucleotides used for preparing the alanine mutant (N428A) | |
| N428A_Sense | gAT ACT gCC ggA gCT gTC CAA AAA gAT (SEQ. ID. No. 15) |
| N428A_Antisense | ATC TTT TTg gAC AgC TCC ggC AgT ATC (SEQ. ID. No. 16) |
| Pair of oligonucleotides used for preparing the lysine mutant (N428K) | |
| N428K_Sense | gAT ACT gCC ggA AAG gTC CAA AAA gAT (SEQ. ID. No. 17) |
| N428K_Anitsense | ATC TTT TTg gAC CTT TCC ggC AgT ATC (SEQ. ID. No. 18) |
| Pair of oligonucleotides used for preparing the tyrosine mutant (N428Y) | |
| N428Y_Sense | gAT ACT gCC ggA TAT gTC CAA AAA gAT (SEQ. ID. No. 19) |
| N428Y_Antisense | ATC TTT TTg gAC ATA TCC ggC AgT ATC (SEQ. ID. No. 20) |

TABLE I-continued list and sequence of the oligonucleotides used
for preparing the PQQ s-GDH mutants according
to the invention.

| Oligonucleotides | sequences |
|---|---|
| Pair of oligonucleotides used for preparing the aspartate mutant (N428D) | |
| N428D_Sense | gAT ACT gCC ggA gAC gTC CAA AAA gAT (SEQ. ID. No. 21) |
| N482D_Antisense | ATC TTT TTg gAC gTC TCC ggC AgT ATC (SEQ. ID. No. 22) |
| Pair of oligonucleotides used for preparing the glutamate mutant (N428E) | |
| N428E_Sense | gAT ACT gCC ggA gAA gTC CAA AAA gAT (SEQ. ID. No. 23) |
| N428E_Antisense | ATC TTT TTg gAC TTC TCC ggC AgT ATC (SEQ. ID. No. 24) |
| Pair of oligonucleotides used for preparing the cysteine mutant (N428C) | |
| N428C_Sense | gAT ACT gCC ggA TgT gTC CAA AAA gAT (SEQ. ID. No. 25) |
| N428C_Antisense | ATC TTT TTg gAC ACA TCC ggC AgT ATC (SEQ. ID. No. 26) |

The nucleic acid molecules coding for the PQQ s-GDH mutants according to the invention can notably be prepared by modifying the nucleotide sequence of the gene coding for the wild-type enzyme of sequence SEQ. ID. No. 1 produced by *Acinetobacter calcoaceticus*. Several techniques for modifying the sequence of the gene are known by a person skilled in the art (see the review by Igarashi et al., Archives of Biochemistry and Biophysics 428 (2004) 52-63). According to a particular manner of preparation, the nucleic acid molecules coding for the PQQ s-GDH mutants according to the invention are prepared by mutagenesis by PCR in the presence of an oligonucleotide bearing the mutation to be introduced (see the example given below).

According to a particular embodiment, the present invention relates to a nucleic acid molecule coding for a PQQ s-GDH mutant according to the invention whose sequence is selected from the group consisting of the sequences SEQ. ID. No. 3, 5, 7, 11 and 13. The nucleic acid molecules coding for the PQQ s-GDH mutants according to the invention can then be cloned into an expression vector such as a plasmid, then transformed in a suitable host such as a bacterium, a yeast or a cell culture.

Expression vector means a vector possessing a region permitting the insertion of a coding nucleotide sequence between the signals that are indispensable for its expression, notably, a promoter (constitutive or inducible), a ribosome attachment site, a transcription termination signal and, optionally, a selection marker such as an antibiotic resistance gene.

The present invention further relates to an expression vector comprising said nucleic acid molecule and to a host cell transformed with said expression vector and expressing a PQQ s-GDH mutant according to the invention.

The expression vector can be introduced into the host cell by any method known by a person skilled in the art, in particular, by altering the membrane permeability of the host cell, for example in the presence of calcium ions, or by electroporation.

After culture of the host cells transformed for expressing a PQQ s-GDH mutant according to the invention, said cells can be recovered by centrifugation, lysed in order to release the enzymes including said PQQ s-GDH mutant according to the invention.

If *Escherichia coli* is the host microorganism, the plasmids that can be are used are notably the plasmids pBluescript, pUC18 or similar.

As examples, the host cells that can be used comprise *Escherichia coli* W3110, *Escherichia coli* C600, *Escherichia coli* JM109, *Escherichia coli* JM101, *Escherichia coli* DH5α, etc.

Preferably, the PQQ s-GDH mutants according to the invention are produced in a strain of *Escherichia coli* JM101; the nucleic acid molecule that encodes them is obtained by modifying the gene of the PQQ s-GDH of *Acinetobacter calcoaceticus* and cloned into the vector pUC18 (Cleton-Jansen et al., Mol. Gen. Genet. 217 (1989) 430-436). The mutants thus produced are exported into the periplasm of the bacterium owing to the signal sequence of PQQ s-GDH. The mutants are then purified after disrupting the bacteria by sonication.

The invention also relates to the use of a PQQ s-GDH mutant according to the invention for determining glucose in solution, i.e. for measuring the concentration of glucose in a sample, notably a biological sample, in particular in blood.

Determination of glucose in solution in a given biological sample can be performed by introducing a redox reagent and a PQQ s-GDH mutant according to the invention into said sample and then comparing the intensity of coloration obtained with standard solutions with a known glucose content.

The present invention also relates to a kit for determination of glucose in solution, characterized in that it comprises a PQQ s-GDH mutant according to the invention.

Typically, said assay kit additionally contains the necessary reagents for carrying out the glucose assay, in particular buffers, any buffer can be used in the kit according to the invention, we may mention non-limitatively phosphate and acetate buffers, buffer with trishydroxymethylaminomethane (TRIS), with N-morpholino-3-propanesulfonic acid (MPOS), with 4-(2-hydroxyethyl)-1-piperazine ethanesulfonic acid (HEPES), buffer comprising a mixture of buffers such as TRIS-acetate etc., the redox reagents can be any reagent for oxidizing the PQQ s-GDH mutant, they can be selected from the group comprising phenazine methosulfate (PMS) in combination with 2,6-dichlorophenolindophenol (DCIP); potassium ferricyanide; ferrocene and complexes derived from ferrocene such as ferrocenemethanol, ferrocene carboxylic acid; and complexes of osmium and ruthenium, standard glucose solutions for constructing calibration curves, and the instructions for use necessary for carrying out the assay.

The present invention further relates to glucose electrodes comprising a conductive material such as a conductive metal, notably platinum, copper, silver, aluminum, gold or steel or carbon, such as vitreous carbon, carbon fibers, carbon nanotube fibers or of diamond etc., said conductive material is covered with a deposit comprising at least one PQQ s-GDH mutant according to the invention; said deposit can further comprise a redox polymer for improving the conductive properties of the conductive material.

The redox polymer is selected from polymers based on ferrocene, osmium and ruthenium and conductive polymers such as polypyrrole and polyananilline.

The methods of immobilization of the PQQ s-GDH mutant on said conductive material can be selected from the conventional methods that are available to a person skilled in the art, which notably comprise inclusion of the PQQ s-GDH mutant in a polymer matrix, adsorption of the PQQ s-GDH mutant on the surface of the polymer membrane, fixation by covalent bonding, or electrodeposition (Gao et al., Chem. Int. ED. 2002, 41, No. 5, 810-813).

Preferably, the immobilized PQQ s-GDH mutant consists of the apoenzyme assembled with the cofactor PQQ; but it is also possible to immobilize the apoenzyme alone and supply the cofactor PQQ additionally, for example in solution in the reaction mixture.

Such electrodes are used advantageously in bioelectric systems such as glucose-based biofuel cells or glucose biosensors.

The present invention thus also relates to a glucose biosensor comprising an electrode according to the invention.

A glucose biosensor consists of an electrode, on which a bioreceptor is immobilized that is capable of recognizing a biological target; binding of the biological target to the bioreceptor leads to physicochemical changes of the membrane and the production of an electrical signal by an electrochemical transducer (amperometric, potentiometric, conductometric, etc.) attached to the electrode; in the present case the bioreceptor is a PQQ s-GDH mutant according to the invention and the biological target is its substrate: glucose.

According to one embodiment, the electrode on which the PQQ s-GDH mutant is immobilized is also covered with a membrane which prevents detachment of said mutant from the electrode. Said membrane can consist of Nafion, cellulose or any biocompatible material, i.e. compatible with a physiological environment.

According to one embodiment of the invention, the glucose biosensor is implanted under the skin and makes it possible to record the blood glucose concentration.

The present invention also relates to biofuel cells using glucose as the source of energy and comprising a first electrode according to the invention as anode and a second electrode as cathode. The cathode can be, for example, an enzymatic electrode that makes it possible to reduce oxygen bearing an enzyme selected from the class of enzymes based on copper (multi copper oxidases) and particularly bilirubin oxidase and laccase. It can also be a metallic electrode, for example of platinum, of gold or of a platinum or gold alloy.

The invention further relates to a method of solution assay of the glucose in a sample comprising the following steps:

a) introducing, into said sample, a redox reagent, reduction of which leads to a change of color, and a PQQ s-GDH mutant, according to the invention;

b) measuring the intensity of coloration of the sample after enzymatic reaction;

c) comparing the intensity of coloration measured in step b) with the intensity measured for standard solutions having a known glucose content;

d) determining the glucose concentration in said sample.

The redox reagent whose reduction leads to a change of color is selected from phenazine methosulfate (PMS) in combination with 2,6-dichlorophenolindophenol (DCIP), potassium ferricyanide, and ferrocene.

The invention also relates to a method of glucose assay of a sample, characterized in that it comprises the following steps:

a) introducing a glucose electrode according to the invention into said sample;

b) measuring the intensity of the current in the sample;

c) comparing the intensity of the current measured in step b) with the intensity measured for standard solutions having a known glucose content;

d) determining the glucose concentration in said sample.

Besides the arrangements presented above, the invention further comprises other arrangements which will become clear from the description given below, referring to examples of application of the present invention, as well as to the appended drawings in which:

FIGURES

FIGS. 1A and 1B are schematics showing the active site of the PQQ s-GDH of *Acinetobacter calcoaceticus*, wild-type (FIG. 1A) or mutated at position Asn428Cys (FIG. 1B). The figure was created with the PyMol software (published by DeLano Scientific LLC, version of 2006) according to the coordinates pdb lcql described by Oubrie et al. (1999). "G" denotes glucose and "PQQ" denotes the coenzyme PQQ. The numbering of the amino acid residues of the active site corresponds to SEQ. ID. No. 2.

FIGS. 2A to 2F are graphs showing the steady-state kinetic parameters in the presence of glucose or maltose:

of the PQQ s-GDH of *Acinetobacter calcoaceticus*, wild-type (WT) and mutated at position 428 by a cysteine (N428C, FIG. 2A);

of the PQQ s-GDH of *Acinetobacter calcoaceticus* mutated at position 428 by a tyrosine (N428Y, FIG. 2B);

of the PQQ s-GDH of *Acinetobacter calcoaceticus* mutated at position 428 by an alanine (N428A, FIG. 2C);

of the PQQ s-GDH of *Acinetobacter calcoaceticus* mutated at position 428 by a lysine (N428K, FIG. 2D);

of the PQQ s-GDH of *Acinetobacter calcoaceticus* mutated at position 428 by an aspartate (N428D, FIG. 2E);

of the PQQ s-GDH of *Acinetobacter calcoaceticus* mutated at position 428 by a glutamate (N428E, FIG. 2F).

EXAMPLES

Figure 1A:
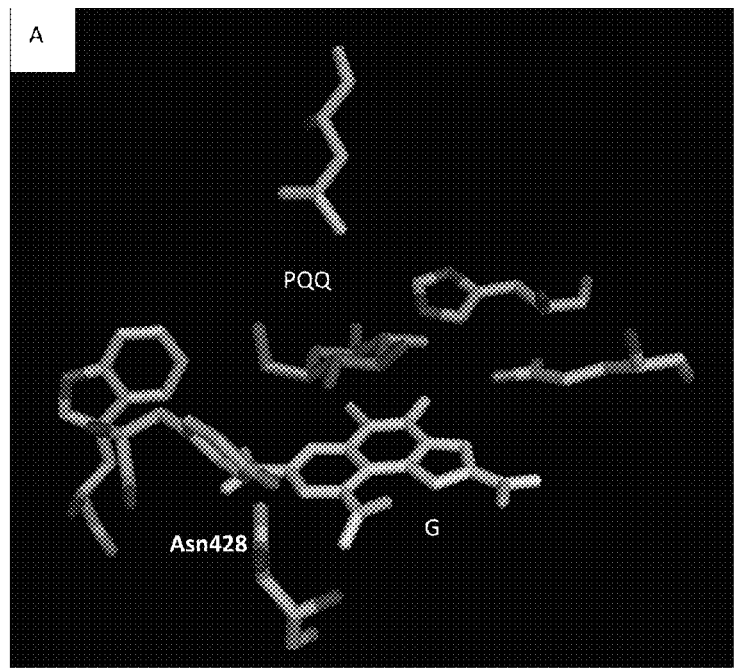
Figure 1B:
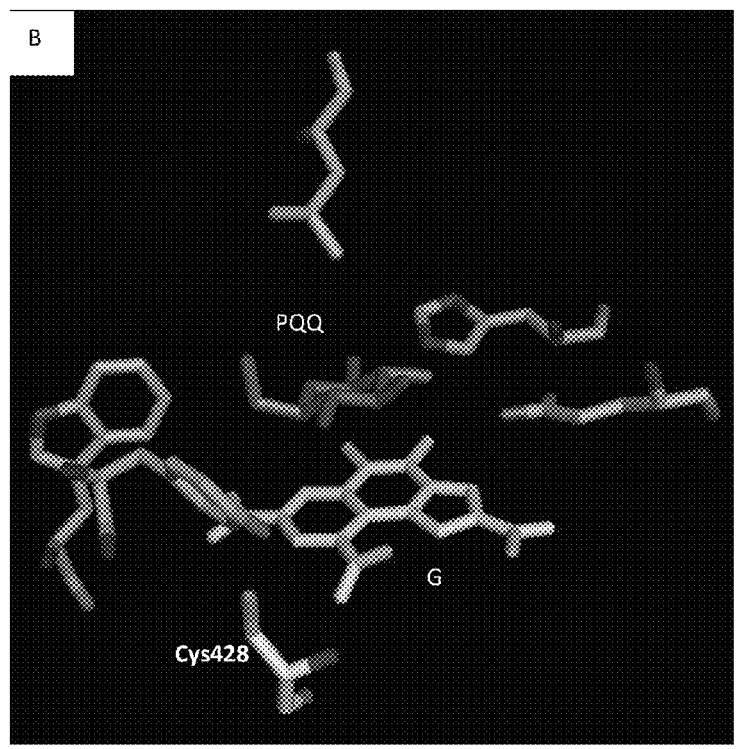
Figure 2A:
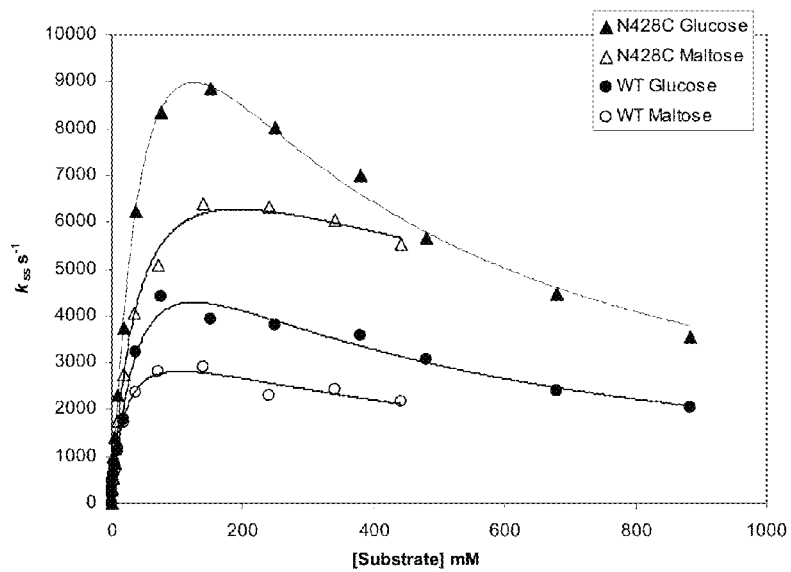
Figure 2B:
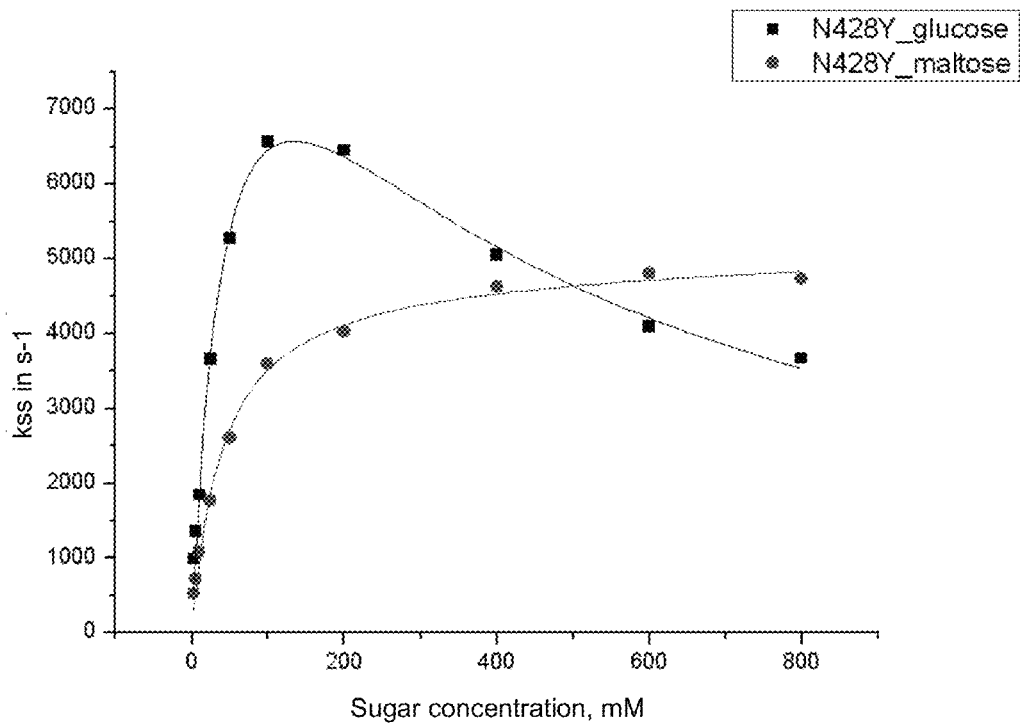
Figure 2C:
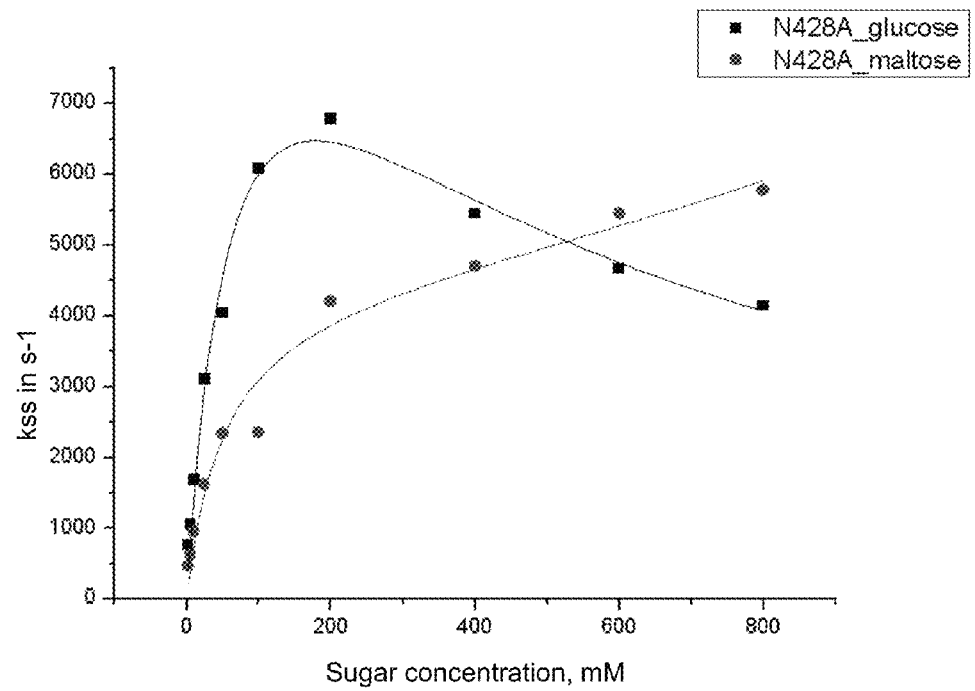
Figure 2D:
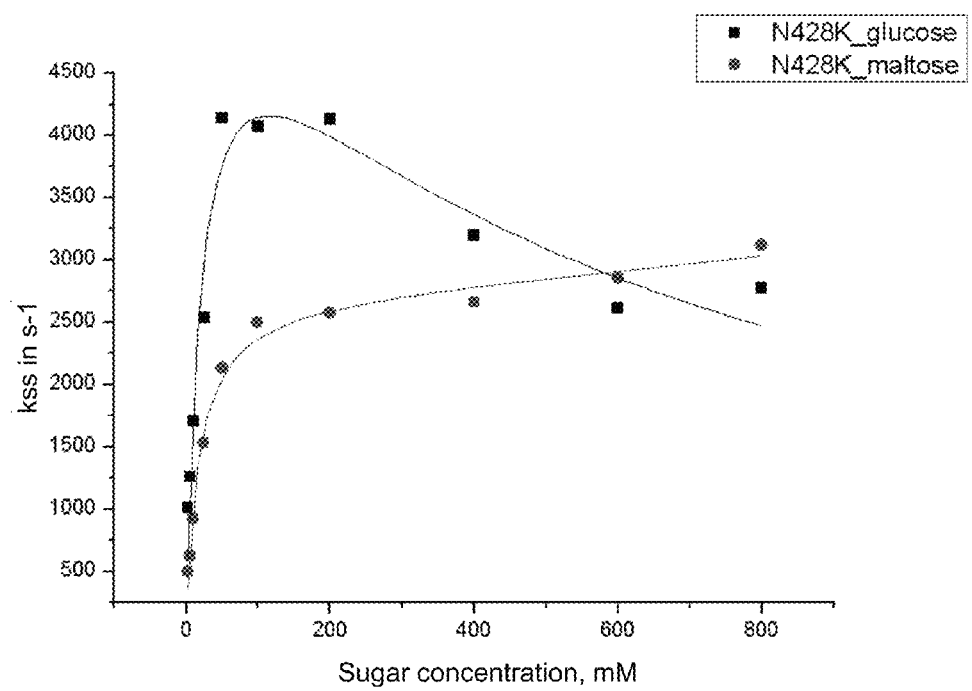
Figure 2E:
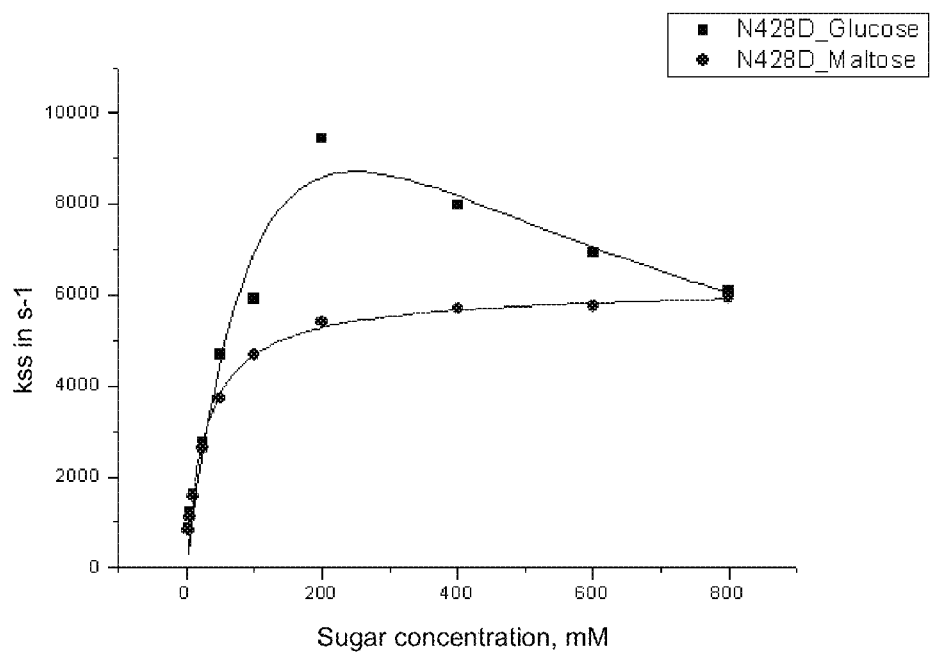
Figure 2F:
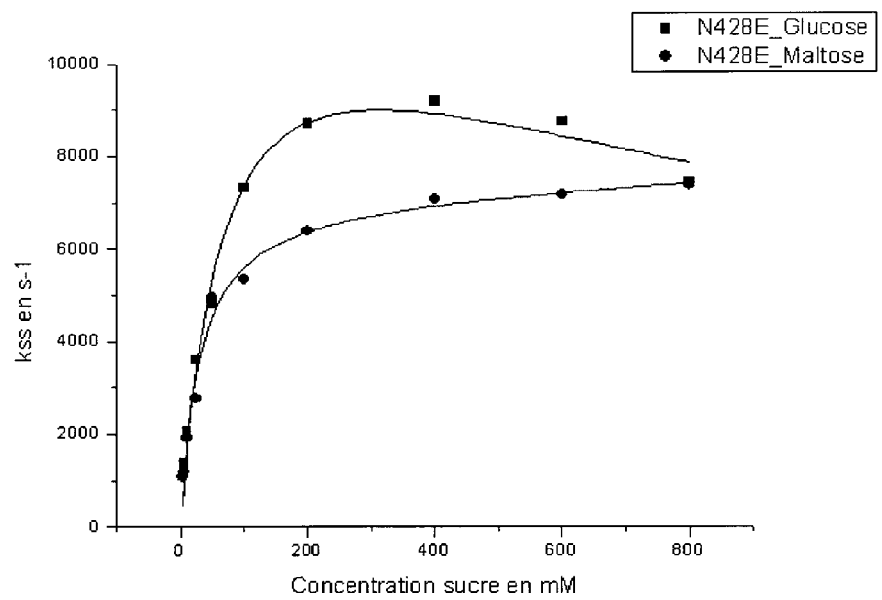

1. Materials 1.1. Bacterial Strains of *Escherichia coli*

$DH_{5\alpha}$: supE44, $\Delta$lacU169, ($\Phi$80 lacZDM15), hsdR17, recA1, endA1, gyrA96, thi-1, relA1 (Hanahan, 1983). This strain is used for plasmid preparation and directed mutagenesis.

JM101: F'traD36 proA$^+$B$^+$ lacI$^q$ $\Delta$(lacZ)M15/$\Delta$(lac-proAB) glnV thi. This strain is used for the production of PQQ glucose dehydrogenase of *Acinetobacter calcoaceticus* in conical flasks. This strain carries the plasmid F-pro-lacI which inhibits expression of the lac promoter.

1.2. Plasmid pgp492: donated by Nora Goosen, recombinant plasmid obtained by cloning the coding sequence of the gene of the soluble PQQ glucose dehydrogenase of *Acinetobacter calcoaceticus* (Cleton-Jansen et al., Mol. Gen. Genet. 217 (1989) 430-436).

1.3. Culture Medium

LB rich medium: tryptone 10 g/L; yeast extract 5 g/L; NaCl 5 g/L; distilled $H_2O$ q.s. 1 L; pH not adjusted, autoclaved for 50 min at 1 bar.

2. Genetic Engineering Techniques

2.1. Transformation of Supercompetent Bacteria

The supercompetent bacteria $DH_{5\alpha}$ are prepared by Inoue's method (Sambrook and Russell (2001). *Molecular Cloning: A Laboratory Manual* (3rd ed.). Cold Spring Harbor Laboratory Press).

2.2. Preparation of the DNA

A plasmid DNA purification kit (Quiagen) is used for the DNA preparations in small and large amounts.

2.3. Sequencing of Double-Stranded DNA

Double-stranded DNA is sequenced with the sequencing kit BigDye Terminator v1.1 or v3.1. The reagent contains the 4 ddNTPs with different fluorescent markers (BigDyeTerminators), AmpliTaq DNA Polymerase, and all other components required for the reaction. The extension products must be purified before being passed through the sequencer ABI 3130xl, to remove the unincorporated markers, salts and other contaminants.

2.4. PCR-Directed Mutagenesis

In the mutagenesis protocol, PCR is performed with the DNA polymerase Pfu of *Pyrococcus furiosus*, six times more faithful than the polymerase Taq for replicating the two strands of the plasmid. The oligodeoxyribonucleotides listed in Table I, each complementary to a strand of the plasmid, will serve as primers for DNA synthesis by the DNA polymerase Pfu, which leads to a plasmid mutated at the non-religated ends.

The amplified product is then treated with the endonuclease Dpn I (target sequence 5'$G^{m6}$ATC-3'), specific to the parent DNA and thus makes it possible to select the neosynthesized DNA containing the mutation. The DNA isolated from most strains of *E. coli* is "methylated DAM" (DAM for DNA adenine methylase; indicates the presence of a methyl on the adenines of the GATC sequences) and can therefore be digested by Dpn I. A fraction of the digestion mixture is used for transforming supercompetent $DH_{5\alpha}$ bacteria, which will religate the ends of the mutated plasmid.

3. Production, Purification and Characterization of the PQQ s-GDH of *Acinetobacter calcoaceticus*

3.1. Production of the Wild-Type and Mutated PQQ s-GDH

The apoenzyme s-GDH is produced in the *E. coli* strain JM101 by the recombinant plasmid pgp492 bearing the sequence coding for the wild-type or mutated s-GDH. A preculture of 50 mL of LB medium supplemented with ampicillin (200 mg/L) (LBA) is seeded by a clone isolated on an LB agar dish supplemented with ampicillin (100 mg/mL) and is stirred at 220 rpm overnight at 37° C. The cultures are seeded at ¹⁄₁₀₀$^{th}$ in LBA medium. They are incubated at 37° C. with stirring (220 rpm) until $OD_{600nm}$ is between 0.4 and 1 $OD_{600nm}$/mL. The cultures are then induced by 400 µM of IPTG and then stirred (180-220 rpm) at 25° C. for 20 h. The cells, collected by centrifugation (5285 g, 4° C.), are washed in a buffer of Tris 20 mM, $CaCl_2$ 3 mM pH 7.5 and stored at −20° C. or at −80° C. without additive.

3.2. Purification of Wild-Type and Mutated Enzymes PQQ s-GDH

3.2.1. Cell Disruption and Treatment with DNase I

The cellular pellet, obtained from a liter of culture, is taken up in 20 mL of buffer Tris 20 mM, $CaCl_2$ 3 mM, pH 7.5 and sonicated at a sonication power of 40 W for 3 minutes with cycling of one second of ultrasound and stopped for one second. The sample obtained, called raw extract, is supplemented with final 2 mM $MgCl_2$ and treated for 30 minutes at room temperature with DNase I (1 U/mL of raw extract). The insoluble cellular debris is then removed from the raw extract by centrifugation at 20000 g for 45 minutes.

3.2.2. Cation Exchange Chromatography

The sonication supernatant, filtered on a filter with a cutoff threshold of 0.22 µm (Millex-GS 0.22 µm, Millipore) and diluted to an $OD_{280nm}$ of 10, is injected onto a cation exchange column source 30S (GE Healthcare®), coupled to the system AKTA purifier (GE Healthcare®), equilibrated in buffer Tris 20 mM, $CaCl_2$ 3 mM, pH 7.5. Elution is performed with a gradient of NaCl from 0 to 1 M in the same buffer at a flow rate of 5 mL/min. The fractions containing the s-GDH protein are combined and concentrated by filtration by centrifugation on Amicon YM10 membrane. At this stage, the s-GDH protein is pure and can be stored at −20° C. in the precipitated form in the presence of ammonium sulfate (90% saturation).

3.2.3 Characterization of the Wild-Type and Mutated s-GDH Enzymes

3.2.3.1. Determination of Molecular Weight

The molecular weight of the monomer of s-GDH after purification is determined by MALDI mass spectrometry. The protein is desalted on a PD10 column (GE Healthcare) and eluted in a buffer of ammonium bicarbonate 50 mM pH 7.5. The lyophilized sample is then analyzed by MALDI-TOF and a molecular weight of 50234.83 Da is found; this molecular weight corresponds to the theoretical molecular weight of the PQQ s-GDH without the signal peptide.

3.2.3.2. Reconstitution of s-GDH with Cofactor PQQ

At the end of purification (buffer Tris 20 mM, $CaCl_2$ 3 mM pH 7.5), the enzyme solution is preincubated for 15 minutes with PQQ at room temperature. The PQQ added corresponds to a final concentration equivalent to twice the molarity of the concentration of enzyme. The excess PQQ is then removed by desalting on a PD10 column (GE Healthcare) equilibrated in a buffer Pipes 20 mM, $CaCl_2$ 3 mM pH 7.

3.2.3.3. Measurement of Concentration

The concentration of enzyme in a solution is calculated from the OD measured at 280 nm, using for the enzyme (dimeric or monomeric), with or without cofactor PQQ, an extinction coefficient of 1.28 or 1.67 $l \cdot g^{-1} \cdot cm^{-1}$ respectively (Olsthoorn et al., 1997).

3.2.3.4. Enzymatic Test

The enzymatic tests are carried out using a Varian spectrophotometer in a buffer of sodium phosphate 20 mM pH 7 at 37° C. in a volume of 3 mL, monitoring disappearance by reduction of DCIP by means of PMS, which acts as electron acceptor, at 600 nm as a function of time. The specific activity of the enzyme is expressed in µmol of DCIP disappeared per minute per mg of protein. The concentrations of PMS and DCIP are 0.6 and 0.06 mM respectively. The enzyme is diluted so as to measure a slope between −0.05 and −0.2 $OD_{600nm}$/min.

4. Techniques for Studying the Enzymatic Properties of the Wild-Type and Mutated PQQ s-GDH

4.1. Determination of the Kinetic Constant ($k_{cat}$) and Michaelis Constant ($K_M$) in the Steady State The experiments are conducted at 37° C. on a Varian spectrophotometer in a buffer of sodium phosphate 20 mM pH 7. The concentration of substrate (glucose and maltose) in the test varies between 0 and 800 mM.

PMS is used as first electron acceptor and the enzyme activity is monitored at 600 nm from the reduction of the DCIP used as second electron acceptor. The initial concentrations of PMS and DCIP are respectively 0.6 and 0.06 mM. The test is started by adding enzyme. The experimental points are analyzed by nonlinear regression with equations 1, 2 or 3 by means of the Sigma-plot 6.0 software according to the following equations:

$$k_{ss} = k_{cat} * [S]/(K_M + [S])\quad\text{(1) Michaelis-Menten model}$$

$$k_{ss} = k_{cat1} * [S]/(K_{M1} + [S]) + k_{cat2} * [S]/K_{M2} + [S])\quad\text{(2) Double hyperbole}$$

$$v/v_{max} = [S]/K_s * (1 + [S]/K_S + [I]/K_I)\quad\text{(3) Michaelis-Menten model with competitive inhibition}$$

Results

The graphs in FIGS. 2A, 2B, 2C, 2D, 2E and 2F show the steady-state kinetic parameters of the soluble PQQ glucose dehydrogenase of *Acinetobacter calcoaceticus*, wild-type (WT) and mutated at position 428 (N428C, N428Y, N428A, N428K, N428D and N428E) in the presence of glucose or maltose.

These results show that, for the two substrates maltose and glucose, the mutated enzymes according to the invention display greater activity than that of the wild-type enzyme; some of these mutants are twice as active as the wild-type enzyme.

4.2. Investigation as a Function of pH

4.2.1. Activity as a Function of pH

Investigation of the variation of the reaction rate constant as a function of pH is performed over a range of pH from 5 to 9 by incubation of the wild-type and mutated enzymes either in a mixed buffer composed of Tris 120 mM, imidazole 30 mM, acetic acid 30 mM (TIA), the ionic strength of which is adjusted to 190 mM with NaCl, or in a buffer of sodium phosphate 20 mM in the pH range from 6 to 8 (NaPi). The experiments are conducted at 37° C. using a Varian spectrophotometer. PMS is used as first electron acceptor at a concentration of 0.6 mM. The activity is monitored by the disappearance of DCIP at 600 nm used as second electron acceptor at a concentration of 0.06 mM. The test is started by adding the enzyme. The optimal activity for the wild-type or mutated enzyme corresponds to 100% and the activity relating to each pH is shown.

Results

Figure 3A:
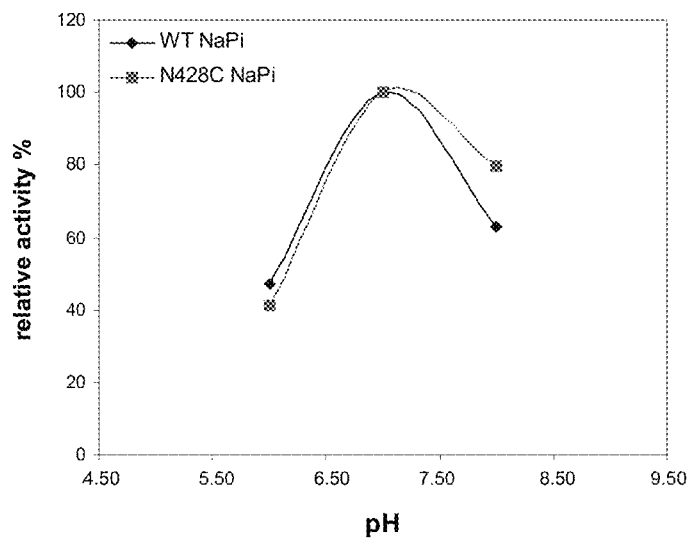
FIGS. 3A and 3B show the activity as a function of pH of the PQQ s-GDH of *Acinetobacter calcoaceticus*, wild-type (WT) and mutated at position 428 by a cysteine (N428C).
Figure 3B:
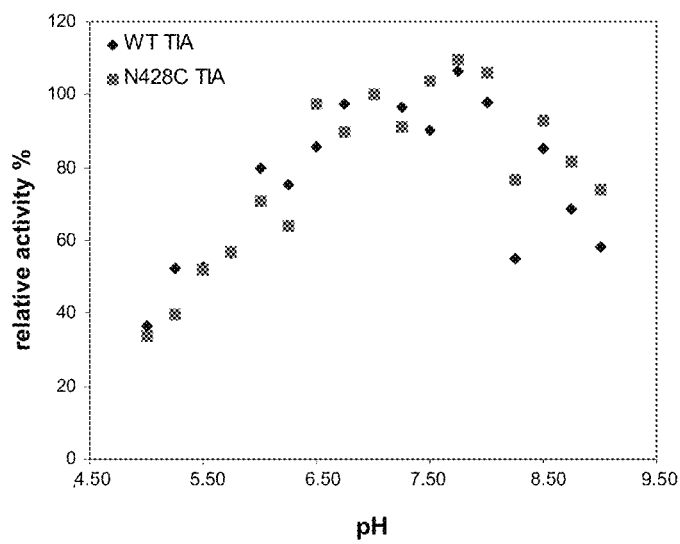

FIGS. 3A and 3B are graphs showing activity as a function of pH, of the PQQ s-GDH of *Acinetobacter calcoaceticus*, wild-type (WT) and mutated at position 428 by a cysteine (N428C). These results show that the cysteine mutant of PQQ s-GDH (N428C) displays a relative activity comparable to that of the wild-type enzyme, demonstrating that the mutation does not lead to a loss of relative activity whatever the pH.

4.2.2. Stability as a Function of pH

The stability as a function of pH of the wild-type or mutated PQQ s-GDH is determined by dilution of the enzyme purified to homogeneity in a mixed buffer in the pH range from 5 to 9. This mixed buffer is composed of Tris 120 mM, imidazole 30 mM, acetic acid 30 mM, the ionic strength of which is adjusted to 190 mM with NaCl. The diluted enzyme solution, between 1 and 6 µg/ml, is preincubated at 37° C. Various samples are taken as a function of time. The residual activity is measured at 37° C. using a Varian spectrophotometer in a buffer of sodium phosphate 20 mM pH 7 in the presence of 0.06 mM DCIP, 0.6 mM PMS. The glucose concentration is 75 mM for testing the wild-type enzyme and 150 mM for testing the mutant N428C.

Results

The mutated enzyme according to the invention displays better stability than the wild-type enzyme whatever the pH and whether this stability is constant over the range of pH tested, in particular, the mutated enzyme remains stable even at pH above 7.

4.3. Investigation as a Function of Temperature

4.3.1. Activity as a Function of Temperature

The variation of the reaction rate constant is investigated as a function of pH in a buffer of sodium phosphate 20 mM pH 7, in the presence of 0.06 mM of DCIP and 0.6 mM of PMS. The glucose concentration is 75 mM for testing the wild-type enzyme and 150 mM for testing the mutant N428C. The temperature varies from 10 to 60° C. The activity is monitored on a temperature-controlled Varian spectrophotometer CARY UV Biomelt. The test is started by adding the enzyme.

Results

Figure 4:
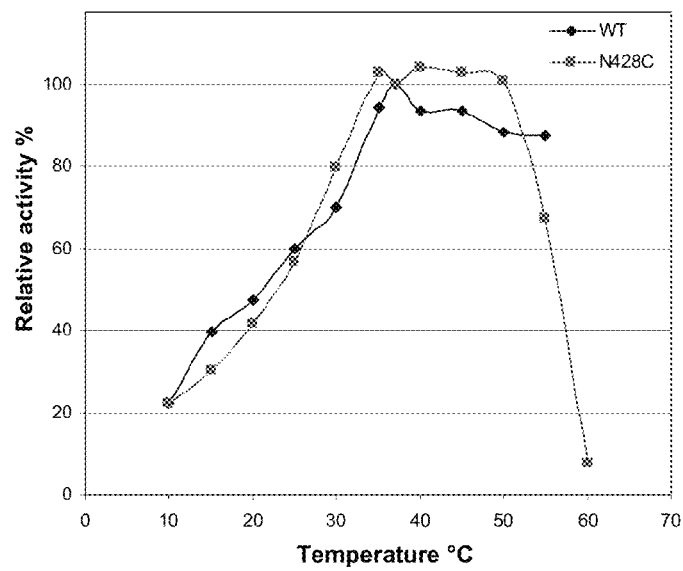
FIG. 4 shows the activity curve of the wild-type (WT) PQQ s-GDH and mutated by a cysteine at position 428 (N428C) as a function of temperature.

FIG. 4 shows the curve of activity of the wild-type (WT) and mutated (N428) PQQ s-GDH as a function of temperature.

This curve shows that between 30 and 50° C., the mutated enzyme displays better activity than the wild-type enzyme.

4.3.2. Stability of the Enzyme as a Function of Temperature

The study is conducted in a buffer of sodium phosphate 20 mM pH 7, in the presence of 0.06 mM of DCIP and 0.6 mM of PMS. The glucose concentration is 75 mM for testing the wild-type enzyme and 150 mM for testing the mutant N428C. The temperature varies from 10 to 60° C. The activity is monitored at 37° C. on a temperature-controlled Varian spectrophotometer CARY UV Biomelt. The test is started by adding the enzyme.

Results

It can be seen that in an incubation time of less than 200 minutes, the mutated enzyme N428C displays better activity at 40 and 50° C. than the wild-type enzyme, thus demonstrating its advantage for blood glucose assay kits.

4.4. Investigation as a Function of the Substrate

The specificity of the cysteine mutant (N428C) was evaluated with respect to various substrates.

The protocol employed for this measurement of specificity is identical to that described in section 4.1., using different substrates.

Figure 5:
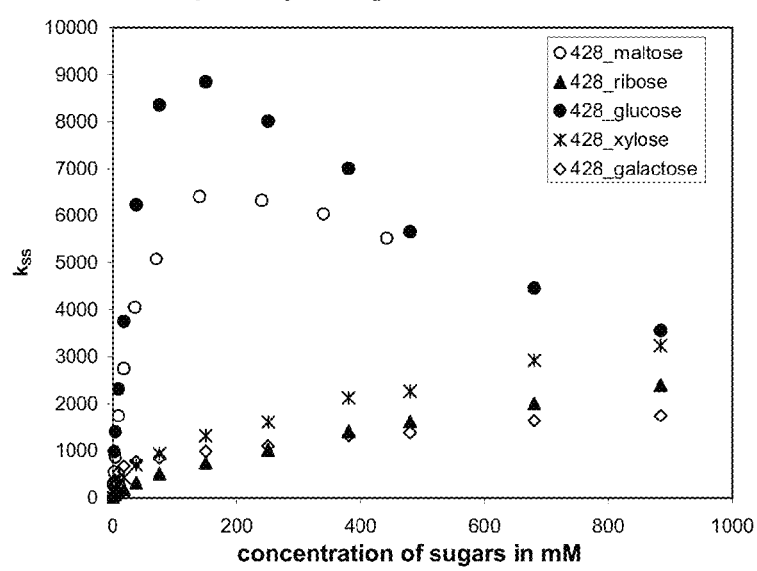
FIG. 5 is a graph showing the activity of PQQ s-GDH mutated at position 428 by a cysteine (N428C) as a function of different substrates.

The results obtained are presented in Table II below and in FIG. 5.

TABLE II

Comparison of the substrate specificity of the PQQ GDH of *Acinetobacter calcoaceticus*, wild-type and mutated comprising a cysteine at position 428 (mutant N428C).

| | WT | | N428C | | |
|---|---|---|---|---|---|
| Substrate | kss s⁻¹ at 4 mM substrate | % Relative activity/WT Glucose | kss s⁻¹ at 4 mM substrate | % Relative activity/ WT | % Relative activity/ N428C Glucose |
| Glucose | 806 | 100 | 1396 | 173 | 100 |
| Maltose | 660 | 81 | 861 | 130 | 61 |
| Ribose | 86 | 10 | 67 | 77 | 4 |

TABLE II-continued

Comparison of the substrate specificity of the PQQ GDH of *Acinetobacter calcoaceticus*, wild-type and mutated comprising a cysteine at position 428 (mutant N428C).

|  | WT | | N428C | | |
| --- | --- | --- | --- | --- | --- |
| Substrate | kss s⁻¹ at 4 mM substrate | % Relative activity/WT Glucose | kss s⁻¹ at 4 mM substrate | % Relative activity/ WT | % Relative activity/ N428C Glucose |
| Xylose | 148 | 18 | 159 | 107 | 11 |
| Galactose |  |  | 357 | 26 | 25 |

Results

Even if the raw values of $k_{ss}$ of the mutant N428C are higher for most substrates than those of the wild-type enzyme; the relative activity, which characterizes the specificity of an enzyme for one substrate relative to another substrate, shows that the mutant N428C is more specific to glucose. Thus, at 4 mM of substrate, with maltose as substrate, a relative activity with respect to glucose of 81% is measured for the wild-type enzyme whereas the mutant N428C displays a relative activity of maltose relative to glucose of 61%.

This same protocol was employed for evaluating the specificity for glucose and for maltose of the aspartate (N428D), glutamate (N428E), alanine (N428A), tyrosine (N428Y) and lysine (N428K) mutants.

The results are presented in Table III below:

|  | N428D | | | N428E | | |
| --- | --- | --- | --- | --- | --- | --- |
| substrate | kss (s-1) at 5 mM substrate | relative activity/ N428D glucose (%) | relative activity/ WT (%) | kss (s-1) at 5 mM substrate | relative activity/ N428E glucose (%) | relative activity/ WT (%) |
| glucose | 1214 | 100 | 150 | 1380 | 100 | 171 |
| maltose | 1103 | 91 | 167 | 1182 | 85 | 179 |

|  | N428A | | | N428Y | | |
| --- | --- | --- | --- | --- | --- | --- |
| substrate | kss (s⁻¹) at 5 mM substrate | relative activity/ N428A glucose (%) | relative activity/ WT (%) | kss (s⁻¹) at 5 mM substrate | relative activity/ N428Y glucose (%) | relative activity/ WT (%) |
| glucose | 1058 | 100 | 131 | 1353 | 100 | 167 |
| maltose | 638 | 60 | 97 | 716 | 52 | 108 |

|  | N426K | | |
| --- | --- | --- | --- |
| substrate | kss (s⁻¹) at 5 mM substrate | relative activity/ N428Y glucose (%) | relative activity/ WT (%) |
| glucose | 940 | 100 | 110 |
| maltose | 625 | 66 | 94 |

---

The invention claimed is:

1. An isolated mutant of pyrroloquinoline-quinone soluble glucose dehydrogenase (PQQ s-GDH) having a percentage identity of at least 90% relative to the PQQ s-GDH of *Acinetobacter calcoaceticus* of SEQ. ID. No. 2, wherein the amino acid located at position 428, referring to SEQ. ID. No. 2, is substituted with an amino acid selected from the group consisting of cysteine, tyrosine, alanine and glutamate, wherein the mutant has an amino acid sequence selected from the group consisting of SEQ. ID. No. 4, 6, 8 and 14.

2. An isolated nucleic acid molecule, coding for a mutant PQQ s-GDH as claimed in claim 1.

3. The nucleic acid molecule as claimed in claim 2, having a sequence selected from the group consisting of SEQ. ID. No. 3, 5, 7 and 13.

4. A recombinant expression vector, characterized in that it comprises a nucleic acid molecule as claimed in claim 2.

5. A recombinant *E. coli* expressing an isolated mutant as claimed in claim 1, characterized in that it is transformed with an expression vector which comprises a nucleic acid molecule, which codes for the mutant PQQ s-GDH.

6. A glucose assay kit, characterized in that it comprises a mutant of PQQ s-GDH as claimed in claim 1.

7. A glucose electrode, characterized in that it comprises a conductive material covered with a deposit comprising at least one mutant of PQQ s-GDH as claimed in claim 1.

8. A glucose sensor, characterized in that it consists of an electrode as claimed in claim 7.

9. A glucose biofuel cell, characterized in that it comprises a first electrode as claimed in claim 7 as anode and a second electrode as cathode.

10. A method of determining glucose in solution in a sample, characterized in that it comprises the following steps:
 a) introducing a redox reagent, reduction of which leads to a change of color, and a PQQ s-GDH mutant as claimed in claim 1, into said sample;
 b) measuring the intensity of coloration of the sample after enzymatic reaction;
 c) comparing the intensity of coloration measured in step b) with the intensity measured for standard solutions having a known glucose content;
 d) determining the glucose concentration in said sample.

11. A method of glucose assay of a sample, characterized in that it comprises the following steps:
 a) introducing a glucose electrode as claimed in claim 7 into said sample;
 b) measuring the intensity of the current in the sample;
 c) comparing the intensity of the current measured in step b) with the intensity measured for standard solutions having a known glucose content;
 determining the glucose concentration in said sample.

* * * * *